(12) United States Patent
Carstens

(10) Patent No.: US 10,612,043 B2
(45) Date of Patent: Apr. 7, 2020

(54) METHODS OF IN VIVO ENGINEERING OF LARGE SEQUENCES USING MULTIPLE CRISPR/CAS SELECTIONS OF RECOMBINEERING EVENTS

(71) Applicant: Agilent Technologies, Inc., Santa Clara, CA (US)

(72) Inventor: Carsten-Peter Carstens, La Jolla, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 45 days.

(21) Appl. No.: 14/773,466

(22) PCT Filed: Jan. 7, 2014

(86) PCT No.: PCT/US2014/010456
§ 371 (c)(1),
(2) Date: Sep. 8, 2015

(87) PCT Pub. No.: WO2014/143381
PCT Pub. Date: Sep. 18, 2014

(65) Prior Publication Data
US 2016/0024529 A1    Jan. 28, 2016

Related U.S. Application Data

(60) Provisional application No. 61/775,510, filed on Mar. 9, 2013.

(51) Int. Cl.
*C12N 15/90* (2006.01)
*C12N 9/22* (2006.01)
*C12N 15/85* (2006.01)

(52) U.S. Cl.
CPC ............. *C12N 15/902* (2013.01); *C12N 9/22* (2013.01); *C12N 15/8509* (2013.01); *C12N 2800/80* (2013.01)

(58) Field of Classification Search
CPC .... C12N 9/22; C12N 15/8509; C12N 15/902; C12N 2800/80
See application file for complete search history.

(56) References Cited

U.S. PATENT DOCUMENTS

2012/0202251 A1* 8/2012 Cornish ................. C12P 19/34
435/91.41
2014/0242702 A1* 8/2014 Chen ..................... C12N 15/907
435/462

FOREIGN PATENT DOCUMENTS

WO    2007025097 A2    3/2007

OTHER PUBLICATIONS

Mali et al. "RNA-Guided Human Genome Engineering via Cas9" Science. Feb. 15, 2013; 339(6121): 823-826.*
Jinek et al. "RNA-programmed genome editing in human cells." Elife. Jan. 29, 2013;2:e00471. (Year: 2013).*
Barras C. "Right on target: New era of fast genetic engineering." https://www.newscientist.com/article/mg22129530-900-right-on-target-new-era-of-fast-genetic-engineering/ accessed Aug. 28, 2018. (Year: 2014).*
Rath, Devashish, et al. "Type IE CRISPR-Cas system as immune system in a eukaryote." bioRxiv (2018): 357301. (Year: 2018).*
Pandika, M. "Jennifer Doudna, CRISPR Code Killer." http://www.ozy.com/rising-stars/jennifer-doudna-crispr-code-killer/4690. accessed Aug. 28, 2018 (Year: 2014).*
Lino et al. "Delivering CRISPR: a review of the challenges and approaches." Drug Deliv. Nov. 2018;25(1):1234-1257 (Year: 2018).*
Dicarlo et al., "Genome engineering in *Saccaromyces cerevisiae* using CRISPR-Cas systems," Nucleic Acids REsearch (Mar. 4, 2013); 41(7):4336-4343.
Cong et al., Multiplex Genome Engineering Using CRISPR/Cas Systems, Science (Jan. 3, 2013); 339 (6121):819-823.
Cho et al., "Targeted genome engineering in human cells with the Cas9 RNA-guided endonuclease," Nature Biotechnology (Mar. 1, 2013); 31(3):230-232.
Kim et al., "Precision genome engineering with programmable DNA-nicking enzymes," Genome Research (Apr. 20, 2012); 22(7):1327-1333.
Dana Carroll, "A CRISPR Approach to Gene Targeting," Molecular Therapy (Sep. 1, 2012); 20(9):1658-1660.

* cited by examiner

*Primary Examiner* — Titilayo Moloye

(57) ABSTRACT

The present invention provides a method for making a large nucleic acid having a defined sequence in vivo. The method combines recombineering techniques with a CRISPR/Cas system to permit multiple insertions of defined sequences into a target nucleic acid at one time, double stranded cleavage of target nucleic acids in which the defined sequences were not successfully inserted, and selection of successful recombinant cells. The method further includes repeating the process one or more times, using a successful recombinant from one round as the host cell for the next round.

9 Claims, 11 Drawing Sheets
Specification includes a Sequence Listing.

FIG. 7

A
Conservation of CRISPR repeat sequence

```
S. pyogenes CRISPR repeat
GTTTTAGAGCTATGCTGTTTTGAATGGTCCCAAAAC
||||||||||||| || |||| |||||| |||||||
GTTTTAGAGCTGTGTTGTTTCGAATGGTTCCAAAAC
S. thermophilus CRISPR repeat
```

B
CRISPR repeat/tracrRNA annealing

S. Pyogenes

```
                    spacer              CRISPR repeat
5'......NNNNNNNNNNNNGUUUUAG-A-GCUAUGCUGUUUGAAUGGUCCCAAAAC 3'
                    ||||||| | |||||||||||||||||||||||||||
3'UUUUUUCGUGCCUAGCCACGGUGAAAAGUUCACUAUACGAUACAAACUUACCAAGUUGUUUUAUAAUAUAUAUGAAAAUA 5'
```

S. thermophilus

```
5'......NNNNNNNGUUUUAG-A-GCUGUGUUGUUUCGAAUGGUUCCAAAAC 3'
                ||||||| | ||||||||||||||||||||||||||
3'UUUUUUCGUGGCUAGCACGGUGAAAAGUUCACACAACAAAGCUUACCAAGUUGGUGUUAAUAUAUAUAUCAAAAU 5'
                    ← tracrRNA 3' hairpin →
```

Design of synthetic spacers for the synthetic tn5 kanR-targeting CRISP array

METHODS OF IN VIVO ENGINEERING OF LARGE SEQUENCES USING MULTIPLE CRISPR/CAS SELECTIONS OF RECOMBINEERING EVENTS

CROSS REFERENCE TO RELATED APPLICATION

This application is a U.S. National Phase of International Application No. PCT/US2014/010456, filed Jan. 7, 2014, which claims priority of U.S. Provisional Application No. 61/775,510 filed on Mar. 9, 2013, the contents of which are incorporated herein by reference in their entirety.

BACKGROUND OF THE INVENTION

Field of the Invention

The present invention relates to the field of molecular biology. More specifically, it relates to methods and nucleic acid constructs for engineering long nucleic acid sequences in vivo using a combination of a recombineering system and a CRISPR/Cas system.

Description of Related Art

Numerous organisms are known in the art that have one or more characteristics, features, or capabilities that have been engineered into them to achieve a certain goal. For example, in view of the potential exhaustion of natural resources, foremost the dwindling petroleum reserves, certain organisms have been genetically modified to quickly and efficiently produce compounds that can replace petrochemicals (for example, "biofuels") in order to provide potential alternatives. Likewise, certain plants have been engineered to be resistant to herbicides, molds, or viruses. As yet another example, plants and microorganisms have been engineered to increase nutritional value or produce bioactive agents, such as pharmaceuticals and biologics.

Recent advances in chemical synthesis of DNA oligomers and their assembly into larger double stranded DNA (dsDNA) structures allow generation of DNA sequences and subsequent controlled manipulation of target organisms essentially at will, a process often referred to in the art as "synthetic biology". Assembly of dsDNA from single stranded DNA oligomers is usually limited to about 1 kilobase (kb) in length due to the low fidelity of the chemical DNA synthesis process. These 1 kb or so segments (sometimes referred to in the art as "parts") are then assembled into larger functional elements of up to about 10 kb in length (sometimes referred to in the art as "devices"). And even larger assemblies up to about 100 kb (sometimes referred to in the art as "systems") are envisioned. However, due to the difficulties in manipulating DNA molecules of 20 kb or greater in length, in vivo host-based technologies will have to be developed or refined to assemble and manipulate "systems".

Aside from the challenges of assembly of large synthetic constructs, the major hurdle in controlled manipulation is the targeted integration and modification of a host genome by the synthetic DNA constructs. Integration into the host genome can be achieved through homologous recombination, a process by which dsDNA is integrated into the host genome at a pre-determined site by virtue of matching sequences (usually several hundred base pairs) between the end of a linear DNA construct and the host genome. With the notable exception of yeast, homologous recombination is an extremely inefficient process. Reasonable homologous recombination frequencies in the bacterial host E. coli require the use of the λ-red/gam or the recE/recT systems.

The bacteriophage-derived λ-red/gam system consists of three components: a 5'-3' exonuclease (λ-exo), a single-strand binding protein (beta), and an inhibitor of the host exonuclease recBCD (gam). The recE and recT genes are encoded in an integrated pro-phage in the E. coli and perform analogous functions to λ-exo and beta, respectively. In a recA+ host cell, integration efficiencies of about $1/10^4$ cells can be achieved, depending on the length of the homologous flanking sequences. The process of λ-red/gam or recET assisted homologous recombination is generally referred to as "recombineering". Unless the recombination event generates a directly selectable phenotype, a selectable marker (usually a drug resistance marker) has to be included in the recombined DNA segment to select for the rare recombinants. The selection marker can be removed at a later stage using a site specific recombinase, such as Flp, if the marker is flanked by site-specific recombination target sites. However, the removal of the selection marker leaves a scar behind (e.g., the site specific recombination site). A popular recombineering system employing these tools has been described by Datsenko and Wanner (1). Despite these improvements, this is still a cumbersome procedure because it requires successively the curing of the λ-red/gam expression plasmid, introduction of the site-specific recombinase plasmid, verification of the loss of the selection marker, and finally the curing of the site-specific recombinase plasmid.

A variant of the recombineering procedure has been developed over the last years based the discovery that, in the presence of λ-gam (a ssDNA binding protein), single stranded DNA oligomers up to 90 nucleotides in length are incorporated into the lagging strand during DNA replication, essentially acting as Okazaki fragments (2). The λ-gam mediated incorporation of the ssDNA oligomers is much more efficient, with rates of greater than 1% achievable, depending on the degree of homology with the template strand (2, 3). However, due to the short sequence modified, the oligomer-directed modifications are only selectable if the resulting mutation generates a directly selectable phenotype.

Even though λ-red/gam and recET are derived from E. coli phages, their utility seems to be transferable to at least some other bacterial hosts, making them potentially universal tools for application in prokaryotes (4, 5).

A new class of nucleic acid targeting systems called CRISPR/Cas has been discovered in prokaryotes that somewhat resemble siRNA/miRNA systems found in eukaryotes. The system consists of an array of short repeats with intervening variable sequences of constant length (clusters of regularly interspaced short palindromic repeats, or CRISPRs) and CRISPR-associated proteins (Cas). The variable sequences located between the short repeat sequences are sequences of infecting viruses (i.e., phages) or foreign plasmids, which have been removed from the virus or plasmid and incorporated into the host genome between the short repeat sequences. The RNA of the transcribed CRISPR arrays is processed by a subset of the Cas proteins into small guide RNAs containing the viral or plasmid sequences, which direct Cas-mediated cleavage of viral or plasmid nucleic acid sequences corresponding to the small guide RNAs. CRISPR/Cas systems are fairly ubiquitous in prokaryotes and seem to be distributed by lateral gene transfer, as some bacteria contain CRISPR/Cas systems but other closely related bacteria do not (for example, E. coli K12 strains carry a CRISPR/Cas system, whereas E. coli B strains do not). The primary function of the CRISPR/Cas system appears to be viral immunity, as most CRISPR encoded targets correspond to bacteriophage genomes (6).

The majority of the known CRISPR/Cas systems guide cleavage of RNA. However, in *Streptococcus thermophilus*, a CRISPR/Cas system (CRISPR3) has been described that directs cleavage of DNA, resulting in double strand breaks within the sequence targeted by the guide RNA (7, 8, 9). The only additional requirement is a 3-4 base pair consensus sequence (GGNG according to (8); TGG according to (9)) located 1 nucleotide 3' (GGNG) or immediately adjacent (TGG) to the guide RNA matching sequence. This sequence is called the protospacer-adjacent motif (PAM). This arrangement prevents self-cleavage of the CRISPR arrays. CRISPR3 can thus act as a programmable restriction enzyme, cleaving selectively at any GGNG (or TGG) sequence located in the appropriate place near a pre-defined target sequence that is complementary to the guide RNA sequence. In an organism with a 50% GC content, CRISPR3-targetable sites are expected every 32 base pairs. This system is transferable to other hosts, as it is functional in *E. coli* (8). The general structure of the *S. thermophilus* CRISPR/Cas9 system is shown in FIG. 1.

The CRISPR/Cas9 system has recently been combined with a recombineering system in *Streptococcus pneumoniae* and *Escherichia coli* to produce mutations at target sites with a high yield of mutants (10). The authors show that two simultaneous mutations at two different target sites can be created using two different guide RNA sequences. According to the authors, selection of successful dual mutants, and the ability to achieve a high efficiency of genome editing, results from co-selection of two selectable markers, enhancement of recombination by the CRISPR/Cas system, and selection against unmutated cells by the CRISPR/Cas system.

SUMMARY OF THE INVENTION

The present invention provides a new method for engineering and/or making nucleic acids in vivo. The method combines recombineering technology with CRISPR/Cas technology to provide a method that allows for multi-site insertion of desired sequences into a nucleic acid target in vivo, creation of long (up to 20 kb or more) engineered nucleic acids in vivo through successive rounds of nucleic acid insertions, and facile selection of recombinants. According to the method of the invention, recombineering techniques are used to insert one or more desired sequences into one or more target nucleic acids at pre-determined sites. The pre-determined sites contain one or more pre-defined cleavage sequences for a dsDNA CRISPR/Cas system, such as the CRISPR/Cas9 system of *S. thermophilus*. Insertion of the desired sequences at the pre-determined sites on the target nucleic acids via recombineering removes the pre-defined cleavage sequences that were present at the sites, whereas a lack of insertion retains the pre-defined cleavage sequences. After the recombineering events, the selected CRISPR/Cas system is used to cleave the target nucleic acids of cells in which all of the expected insertion events did not occur, as those nucleic acids still have one or more intact cleavage sites. Cleavage at these unaffected sites results in death to the cell, or at least to a high enough percentage of non-recombinant cells in a population of treated cells, which allows for easy identification and selection of desired recombinant cells (i.e., cells in which the desired sequences have been inserted into the target nucleic acid). Selected recombinant cells are then subjected to one or more subsequent rounds of insertion/cleavage/selection. During the subsequent rounds, insertion of desired sequences at pre-determined sites on the target nucleic acids results in removal of pre-defined cleavage sequences that are different in sequence, and thus different in cleavage specificity, than the cleavage sequences of the immediately preceding round. Further, during these subsequent rounds, there is at least one round, and preferably multiple rounds, in which a pre-determined site for insertion of a desired sequence contains a nucleotide sequence that was part of a previously-inserted desired sequence. Through use of multiple rounds of targeted insertion of desired sequences and selection for successful recombinant cells, the present method provides a robust way to engineer, in vivo, large nucleic acid constructs at a high efficiency. The method also provides a *facile* selection scheme to produce in vivo engineered nucleic acids having multiple site-specific alterations, to identify recombinant cells, and to eliminate non-recombinant cells.

The present invention provides a recombineering method combined with a CRISPR/Cas cleavage method that is capable of cleaving dsDNA, such as the CRISPR/Cas9 DNA cleaving system of *S. thermophilus*. The present method allows direct selection of one or multiple independent simultaneous recombineering events without the need for integrated selection markers. The ability to directly select for multiple independent scarless recombination events enables direct, in vivo assembly of large synthetic sequences (e.g., devices and systems) without the need to attempt to manipulate large sequences in vitro. In addition, the present invention avoids the cumbersome techniques of other recombineering methods, which require curing of a λ-red/gam expression plasmid, introduction of a site-specific recombinase plasmid, verification of the loss of a selection marker, and curing of the site-specific recombinase plasmid.

The invention also provides a recombinant, engineered, or otherwise non-naturally occurring CRISPR/Cas system. Typically, the system is provided in the form of one or more nucleic acids containing one or more components. Although in these embodiments the system can be provided on multiple nucleic acids, preferably the system is provided on a single nucleic acid, such as a delivery and/or expression vector. In other embodiments, some of the components are provided in the form of nucleic acid, while other components are provided in the form of protein. In some exemplary embodiments, the system is provided as a ready-to-use combination comprising a component for enzymatic cleavage of a target double-stranded nucleic acid at a cleavage sequence, such as the Cas9 protein of *S. thermophilus*, and a processed form of a CRISPR array, which includes a processed spacer or guide RNA. In certain embodiments, a tracr RNA is also provided, either as a separate component or as an element fused to the spacer RNA. The tracrRNA can be defined as a short, non-coding RNA that is required for processing of the crRNA into short guide RNA and for CAS-mediated cleavage of the target DNA. The tracrRNA has a section that anneals to the CRISPR repeat to initiate processing by the host enzyme RNAse III. As currently understood, the primary sequence of the CRSIPR repeats of the CAS9 system are of minor importance. What matters more is the structure formed by annealing of the tracrRNA to the CRISPR repeat (e.g., the differences between the CRSIPR sequences of different CAS9 systems are matched by a corresponding difference in their tracrRNA). There are several thousand different CRISPR systems known, most with a specific CRSIPR repeat sequence (a database can be found at this web address: http double forward slash crispr.u-psud.fr/). More specifically to the CAS9 (e.g., DNA targeting) systems: a homology search of the *S. thermophilus* Cas9 coding sequence identifies greater than 300 matches. Due to relative good level of conservation, one would infer that most of the other systems target DNA as well. A spot check demonstrates that there is quite a bit of deviation in the actual CRISPR sequences. However, it appears that the overall structure of the annealed tracrRNA/CRISPR RNAs is conserved.

In other exemplary embodiments, the system is provided on a single, dsDNA plasmid vector. The system in these embodiments in general includes: i) a component for enzymatic cleavage of a target double-stranded nucleic acid at a cleavage sequence; ii) a CRISPR array component that comprises a nucleic acid sequence that includes two or more repeat sequences and one or more spacer sequences (the spacer sequences are also referred to herein at times as "guide sequences" to reflect their function in directing a cleavage assembly to the correct cleavage sequence), the repeat sequences and spacer sequences being arranged in alternating order starting with a repeat sequence; and iii) a tracr component. The CRISPR array and tracr components are provided in the form of nucleic acid, while the component for enzymatic cleavage can be provided in the form of nucleic acid or protein. Preferably, the component for enzymatic cleavage is provided in the form of nucleic acid. Preferably, the nucleic acid for all embodiments is DNA, and especially dsDNA. Preferably, the CRISPR array and tracr components are provided in a form containing sequences sufficient for transcription of at least a portion of each component's sequence within a host cell. Where the component for enzymatic cleavage is provided in the form of nucleic acid, the component is preferably provided in a form containing sequences sufficient for transcription of at least a portion to generate a messenger RNA, and for translation of the messenger RNA into a protein having double-stranded nucleic acid, and preferably dsDNA, cleaving activity, within a host cell. According to the system of the invention, the CRISPR array component comprises at least one spacer sequence that has sufficient identity with a cleavage sequence on the target nucleic acid to direct the guide sequence, when bound to the enzyme of component ii) and the tracr component, to the cleavage sequence to permit cleavage of the cleavage sequence by the enzyme. In embodiments, the CRISPR/Cas system is isolated or purified, at least to some extent, from cellular material of a cell in which it was produced.

In some exemplary embodiments, the CRISPR array component comprises a single spacer sequence, although it can be present in multiple copies within the array. In these embodiments, the spacer sequence is not a wild-type sequence of the CRISPR array from which it is derived, but instead is an engineered sequence having specificity for a known, pre-defined cleavage sequence on a target nucleic acid that is different than the target sequence for the wild-type spacer sequence. In these embodiments, the CRISPR/Cas system (e.g., one expressed from a plasmid construct introduced into a host cell by way of transformation) can be used to select for one or multiple recombineering events that eliminate a single pre-defined cleavage sequence present on a target nucleic acid.

In some exemplary embodiments, the CRISPR array component comprises at least two spacer sequences, wherein one or more of the spacer sequences are not wild-type sequences of the CRISPR array from which they is derived, but instead are engineered sequences having specificity for known, pre-defined cleavage sequences on a target nucleic acid. In some embodiments, all of the spacer sequences are engineered sequences, which are engineered to target two or more cleavage sequences on a target nucleic acid, all of which are different than those targeted by the wild-type CRISPR array. In this way, a single CRISPR/Cas system can be used to select, in a single round of selection, integration of multiple, different recombineering segments into a target nucleic acid, which result in removal of multiple, different pre-defined cleavage sequences.

In another aspect, the invention provides recombinant cells that contain a CRISPR/Cas system according to the invention. For example, in embodiments, the invention provides recombinant cells that contain an expression plasmid comprising a CRISPR array that includes at least two spacer sequences, wherein at least one of the spacer sequences is a sequence engineered to target a pre-defined cleavage site on a target nucleic acid. The recombinant cells of the invention have many uses, but in exemplary embodiments, they are used to create, in vivo, large (i.e., long) or extremely large engineered sequences. Typically, the recombinant cells are prokaryotic cells, such as those commonly used in the field of molecular biology.

In a related aspect, the invention provides recombinant cells that contain a target nucleic acid that has been engineered in vivo to have a large or extremely large sequence using the method of the present invention. As the skilled artisan will recognize, the particular sequence of each large or extremely large sequence will vary based on the desires of the practitioner. Thus, the sequence is not a limiting or critical factor in practicing the invention. Indeed, it is an advantage of the invention that any number of engineered sequences can be constructed using the method of the present invention.

In yet another aspect, the invention provides a molecular biology kit. While the kit of the invention have many applications, in general, a kit according to the invention will comprise some or all of the components, reagents, etc. used to create, in vivo, large or extremely large engineered sequences by way of multiple rounds of recombineering/cleavage/selection, as disclosed herein. The term "kit" is a term of art. As such, the skilled artisan will immediately understand the appropriate materials, shapes, sizes, etc. for fabricating a kit according to the invention and for containing or packaging components, reagents, etc. of the kit without those materials, shapes, sizes, etc. needing to be disclosed herein.

In an exemplary embodiment, a kit according to the invention contains one vector (e.g., a delivery and expression plasmid) comprising a CRISPR/Cas system that is designed for, and specific for, one or more pre-defined cleavage sequences on a target nucleic acid so as to effect selection of multiple recombineering events in a single round of recombineering/cleavage/selection, which, when successful, i) eliminates multiple occurrences of a single pre-defined cleavage sequence on the target nucleic acid, ii) eliminates single or multiple occurrences of two or more pre-defined cleavage sequences on the target nucleic acid, or iii) both. In another exemplary embodiment, a kit according to the invention contains two or more vectors, preferably packaged separately, comprising CRISPR/Cas systems, as disclosed herein. Each vector (i.e., each CRISPR/Cas system) is designed for, and specific for, one or more pre-defined cleavage sequences on a target nucleic acid so as to effect selection of multiple recombineering events in a single round of recombineering/cleavage/selection, which, when successful, i) eliminates multiple occurrences of a single pre-defined cleavage sequence on the target nucleic acid, ii) eliminates single or multiple occurrences of two or more pre-defined cleavage sequences on the target nucleic acid, or iii) both. The vectors are designed such that none of the CRISPR array spacer sequences of one vector target a single same pre-defined cleavage sequence of a vector designed to be used in a recombineering/cleavage/selection round practiced immediately prior to the round in which the vector is to be used. In other words, each vector is designed with the understanding that, if used in a method according to the present invention, no spacer sequence should be specific for the same pre-determined cleavage sequence of an immediately prior round of practice of the method. That is, because the immediately prior round of practice of the invention will have eliminated all occurrences of the pre-defined sequence, the vector will fail to provide an adequate selection mechanism for the current round of practice of the invention. Further, and importantly, the invention contemplates introducing, in the second round, one or more occurrences of a pre-defined cleavage sequence that was a target of the first round. In embodiments capturing this concept, the number of vectors and engineered spacer sequences can be minimized. For example, a kit according to the invention can comprise two vectors, one having one or more engineered spacer sequences specific for one or more pre-defined cleavage sequences for odd rounds of practice of the invention, the other vector having one or more engineered spacer sequences specific for one or more pre-defined cleavage sequences for even rounds of practice of the invention. When used in combination with recombineering segments that contain either even-round pre-defined cleavage sequences (for practicing the method on odd rounds) or odd-round pre-defined cleavage sequences (for practicing the method on even rounds), the kit can be useful in creating, in vivo, long engineered constructs of defined and desired sequence.

In another aspect, which flows from the disclosure herein, the invention provides methods of making, in vivo, a recombinant cell having a large or extremely large engineered sequence, which can comprise only exogenous-derived (i.e., engineered, recombinant, non-natural) sequence or can comprise a mixture of exogenous-derived sequence and natural sequence. For example, the present invention allows for production of large and extremely large engineered sequences in vivo. However, there are times in which a particular native or wild-type sequence will want to be conserved (e.g., a promoter sequence, a metal binding site, an enzymatically active domain or pocket). The invention recognizes this situation and allows for retention of the sequence (although the invention also recognizes that it is essentially as easy to replace the original sequence with an identical engineered sequence).

In another aspect, which also flows from the disclosure herein, the invention provides recombinant cells created by methods disclosed herein. For example, the invention provides prokaryotic (e.g., eubacterial) recombinant cells that contain one or more CRISPR/Cas systems of the invention. Likewise, the invention provides recombinant cells that contain one or more CRISPR/Cas systems of the invention and further comprise a recombineering construct and/or a construct that provides the necessary components to effect recombineering in a given host cell. Other aspects will be apparent to the skilled artisan based on the present disclosure.

BRIEF DESCRIPTION OF THE DRAWINGS

The accompanying drawings, which are incorporated in and constitute a part of this specification, illustrate embodiments of the invention, and together with the written description, serve to explain certain principles of the invention. The drawings are provided to assist the reader in understanding elements and features of embodiments of the invention, and should not be construed as limiting the invention in any way.

DETAILED DESCRIPTION OF EXEMPLARY EMBODIMENTS OF THE INVENTION

Figure 1:
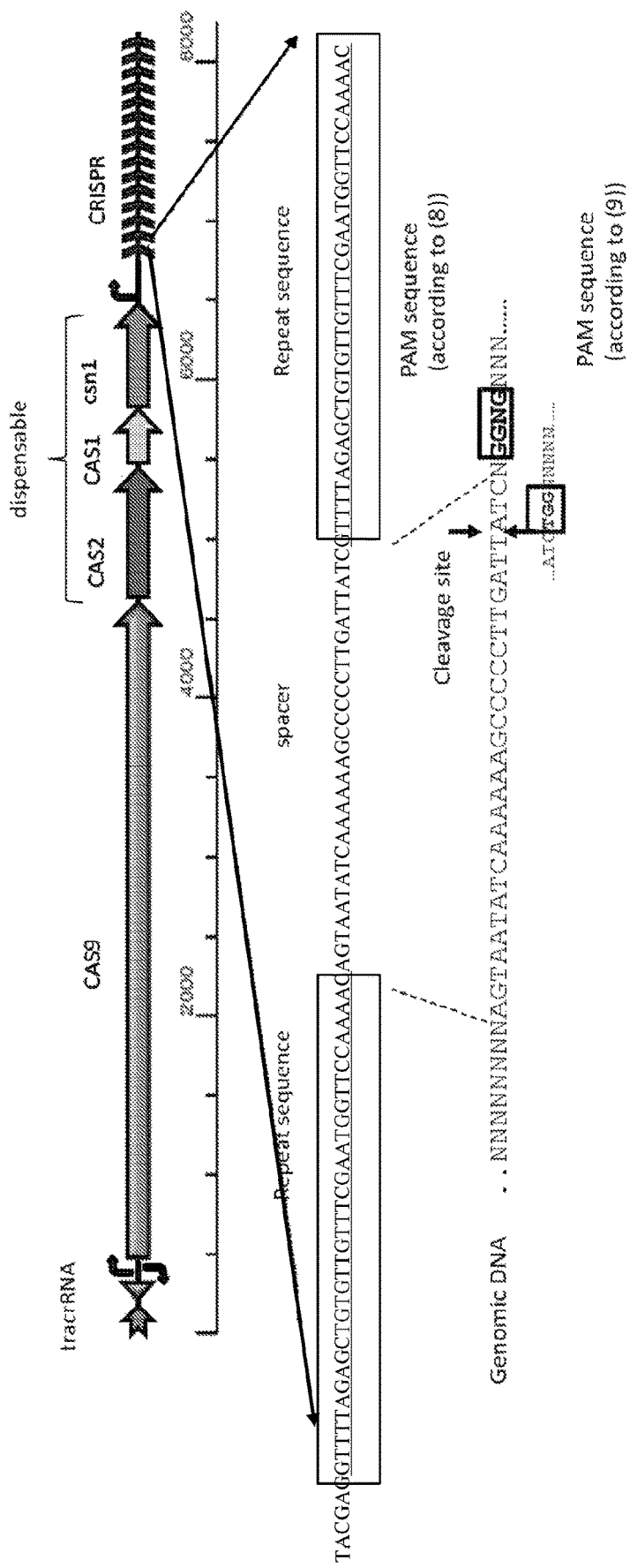
FIG. 1 is a diagram of the natural CRISPR/Cas9 system of S. thermophilus. The figure shows that the system consists of four protein coding sequences (CAS9, CAS1, CAS2, and csn1) and two non-coding RNAs, the CRISP array and the tracrRNA. The CAS1, CAS2, and csn1 encoded proteins are thought to be involved with the acquisition of new protospacers for the CRISPR unit and are dispensable for CRISPR/Cas9 mediated target cleavage. The CRISPR array, a segment of which is shown (SEQ ID NO: 1), consists of short 34 nucleotide (nt) repeats (SEQ ID NO: 2) and 30 nt intervening sequences ("spacers" or "guide sequences," SEQ ID NO: 3) that correspond to the cleavage sequences on a target nucleic acid, which is typically dsDNA. The target DNA (SEQ ID NO: 4 or 7) is cleaved by Cas9 if a Proto-spacer Adjacent Motif (PAM) sequence (SEQ ID NO: 5 or 6) is present 3' to the spacer sequence. PAM sequence has been substantially investigated in e.g., (10) and is known in the art. An additional non-coding RNA species (tracrRNA) has been identified as a required element for CRISPR RNA processing and CRISPR/Cas9-mediated dsDNA cleavage.

Reference will now be made in detail to general aspects and various exemplary embodiments of the invention, examples of which are illustrated for non-limiting descriptive purposes in the accompanying drawings. It is to be understood that the following discussion of exemplary embodiments is not intended as a limitation on the invention, as broadly disclosed herein. Rather, the following discussion is provided to give the reader a more detailed understanding of certain aspects and features of the invention.

Unless defined otherwise, all technical and scientific terms used herein have the same meaning as commonly understood by one of ordinary skill in the art to which the term belongs. Although any methods and materials similar or equivalent to those described herein can be used in the practice of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a nucleic acid" includes a plurality of such nucleic acids and reference to "a pre-defined cleavage sequence" includes reference to one or more such sequences and equivalents thereof known to those skilled in the art, and so forth. Furthermore, the use of terms that can be described using equivalent terms include the use of those equivalent terms. Thus, for example, the use of the term "plasmid" is to be understood to include the terms "linear nucleic acid", "phagemid", "phage", and other terms used in the art to indicate a nucleic acid for delivering nucleic acids to a cell, or to an extrachromosomal element.

In general, the present invention provides a method based on a combination of recombineering technology and dsDNA cleaving technology of the CRISPR/Cas type.

The recombineering technology allows for insertion of nucleic acids of desired sequence and length into specific sites into the genome of a host cell or other target nucleic acid (based on homologous recombination events via recombineering), while the CRISPR/Cas system allows for selection of recombinant cells that have had their genomes (or other target nucleic acids) modified by incorporation at pre-determined sites of the desired sequences. Unlike previous work reported in the literature, the present invention is not simply directed to selection of recombinant cells that have undergone a mutagenesis event, or to creation of recombinant cells having been subjected to multiple, independent mutagenesis events. Rather, the present invention is directed to creation of multiple, independent changes (i.e., mutations) in a target nucleic acid, preferably at the same time, selection of recombinant cells having the desired mutations, and subjecting the recombinant cells to one or more subsequent rounds of recombination and selection, wherein at least one of the rounds involves recombineering using homologous recombination between a sequence present on a recombineering segment and a sequence present on a recombineering segment used in a previous round, such as a sequence present in a desired sequence introduced into the target nucleic acid during a previous round. Multiple rounds of insertion/cleavage/selection, and linking of inserted desired sequences during successive rounds, enable the in vivo production of large (i.e., 10 kb, 20 kb, 30 kb, 50 kb) and even extremely large (i.e., in excess of 50 kb) engineered sequences. While not being limited to any particular function, the engineered sequences can encode a set of functionally related proteins, such as those involved in a biochemical pathway, for example a pathway that produces, uses, or is involved in the metabolism of: biofuels, sugars, proteins, carbohydrates, fat, a nutritionally balanced foodstuff; or that confers resistance to an insect or a herbicide. The present method further allows direct selection of one or several independent simultaneous recombineering events over two or more rounds of insertion/cleavage/selection without the need for integrated selection markers or the removal of markers upon completion of the engineering. The ability to directly select for several independent scar-less recombination events enables direct, in vivo assembly of large and extremely large synthetic sequences (e.g., devices and systems) without the need manipulate large sequences in vitro.

In summary, the method of the invention comprises: identifying or creating a dsDNA CRISPR/Cas cleavage sequence at a pre-determined site on a target nucleic acid in a host cell; obtaining a recombineering segment for the pre-determined site, where the recombineering segment comprises a sequence that is desired to be inserted into the target nucleic acid and that, when inserted into the target nucleic acid by homologous recombination, destroys (e.g., removes) the cleavage sequence; introducing into the host cell the recombineering construct; if not already present in the host cell, introducing into the host cell a nucleic acid encoding a CRISPR/Cas system that is specific for the cleavage sequence; maintaining the cell in a viable state until recombineering insertion of the desired sequence and CRISPR/Cas cleavage of the cleavage site has occurred; selecting for recombinant cells that survive the CRISPR/Cas cleavage event; and subjecting a selected recombinant cell to one or more additional rounds of recombineering/cleavage/selection. In preferred embodiments, each recombineering/cleavage/selection round targets multiple pre-defined cleavage sequences having the same sequence, multiple pre-defined cleavage sequences, each having different cleavage sequences, or a combination of both. As such, for each round of the method that is practiced, each pre-defined cleavage sequence is different than each pre-defined cleavage sequence used in the immediate previous round.

Further, according to preferred embodiments of the method of the invention, at least one round of recombineering uses as a target sequence for recombination a nucleotide sequence present on a recombineering segment that was used in a previous round of recombineering, and which was introduced into the target nucleic acid as a result of a previous round of recombineering/cleavage/selection. In other words, for at least one of the second through $n^{th}$ rounds of recombineering/cleavage/selection, at least one recombineering segment includes a sequence that can homologously recombine with a sequence that was present on a recombineering segment, and in embodiments a desired sequence, that was introduced into the target nucleic acid in a previous round. In some rounds, recombineering occurs such that two previously-introduced desired sequences are joined by way of homologous recombination with a third desired sequence, thus resulting in a long, fully engineered sequence in the target nucleic acid. Using the method of the present invention, large or extremely large engineered nucleic acids can be produced in vivo by successive rounds of recombineering/cleavage/selection.

In embodiments, to achieve extremely large engineered nucleic acids, in one or more rounds some or all of the recombineering segments are engineered to include a pre-defined cleavage sequence, which can serve as a selection site for a future cleavage event. In embodiments, the pre-defined cleavage sequence is engineered in the desired sequence portion of the segment. In other embodiment, the cleavage sequence is engineered in the sequence involved in recombination. In yet other embodiments, the cleavage sequence is engineered to bridge the two sequences on the recombineering segment.

The method of the invention includes identifying or creating a dsDNA CRISPR/Cas cleavage sequence at a pre-determined site on a target nucleic acid. Typically, for at least the first round, the target nucleic acid site is a site on a host cell genome, as typically most of the stable dsDNA nucleic acid in a cell is considered a part of the cell's genome. Examples of host cell genomic dsDNA include, but are not necessarily limited to, a host cell chromosome and a stably maintained plasmid. However, it is to be understood that the present method can be practiced on other dsDNA present in a host cell, such as non-stable plasmid DNA, viral DNA, and phagemid DNA, as long as there is a means for obtaining the dsDNA after each round that the method is practiced. In prokaryotes, removing Cas-specific cleavage sites on a host cell chromosome through recombineering prevents lethal cleavage of the chromosome. Likewise, removing one or more Cas-specific cleavage sites on an extrachromosomal element (e.g., plasmid) that confers viability under certain selective pressures (e.g., antibiotic resistance) to a prokaryote through recombineering prevents cleavage of the extrachromosomal element and death to the cell when exposed to the selective pressure. Further, recombineering/cleavage/selection can not only be used to engineer nucleic acid constructs of interest, but the recombineering events can be used to create, repair, or destroy secondary sequences, which confer viability or cause cell death under selective pressures (e.g., temperature sensitivity, nutrient requirement, antibiotic resistance). Regardless of the nature of the host cell dsDNA, as successive rounds of the method are practiced, less and less of the host cell dsDNA is present on the target nucleic acid, and more and more engineered sequence is present. Therefore, in this document, the target is simply referred to as "target nucleic acid" without consideration of the amount of native or engineered sequence present on the target.

The method of the invention involves at least two rounds of recombineering/cleaving/selecting. Therefore, at least two different pre-defined cleavage sequences in the target nucleic acid must be identified or created. It is known in the art that cleavage sequences for natural CRISPR/Cas systems exist, and that these sequences vary from organism to organism and from strain to strain. The key sequences for successful targeting and cleavage appear to be the spacer sequence (much of the sequence of which may vary), and in particular the 12 or so nucleotides on the 3' end of the spacer sequence, and the PAM sequence (which should be organism-specific). The spacer sequence allows for identification of the sequence to cleave (i.e., in a natural system, non-native DNA), while the PAM and 3' spacer end sequences allow for specificity and activity. In view of the general knowledge regarding various known CRISPR/Cas systems, it is a simple matter to select a system, and identify or engineer a target cleavage site for that system. As mentioned above, different cleavage sites, which are dictated by spacer sequences in the CRISPR array, can be used in different rounds to effect differential cleavage and differential selection from round to round.

Typically, the method is practiced in a given round using a single CRISPR/Cas system, e.g., the CRISPR/Cas9 system of *S. thermophilus*. However, it should be recognized that the method is not limited to cleavage of a single pre-defined cleavage sequence (regardless of how often it occurs in the target nucleic acid), but instead allows for targeted cleavage of multiple pre-defined cleavage sequences, which can be present in any number of copies in the target nucleic acid. This feature is enabled by the fact that multiple, different spacer sequences can be engineered into a CRISPR array, and that each spacer sequence can be specific for a different pre-defined cleavage sequence. Further, an entire CRISPR array can be transcribed by cellular machinery, providing a transcript having all of the spacer sequences. The transcript can then be processed to release each individual spacer sequence. Having a knowledge of the sequence of the target nucleic acid allows the practitioner to identify (and, if necessary, create) a wide variety of pre-defined cleavage sequences for a given CRISPR array.

In other embodiments, one or more rounds of recombineering/cleavage/selection uses a CRISPR/Cas system that is different from one or more other rounds. There are no particular considerations to address between the various dsDNA CRISPR/Cas systems, and the practitioner is free to select a desired system as a matter of design choice. The only limitation is that, for any round, the pre-defined cleavage sequences, and thus the spacer sequences, must not be the same as those used in the immediately previous round.

In one embodiment, the invention provides a method for engineering, in vivo, a nucleic acid having a desired sequence, said method comprising:

a) obtaining a double stranded plasmid containing the sequence for a recombineering segment flanked on each end by a cleavage site for a pre-selected double stranded DNA cleaving CRISPR/Cas system, the orientation of one cleavage site on the plasmid being opposite to the orientation of the other cleavage site, wherein the recombineering segment has sufficient identity with a pre-determined site on a target nucleic acid in a host cell to participate in homologous recombination with that site via recombineering, and wherein the recombineering segment comprises a sequence that is desired to be inserted into the target nucleic acid and that, when inserted into the target nucleic acid by homologous recombination via recombineering, eliminates a cleavage sequence that is different than the cleavage sequence for excision of the recombineering segment from the double stranded plasmid;

b) introducing into one or more host cells the recombineering plasmid of a);

c) if not already present in the host cells, introducing into the host cells a nucleic acid encoding a CRISPR/Cas system that is specific for the recombineering plasmid cleavage sequence;

d) if not already present in the host cells, introducing into the host cells a nucleic acid encoding a CRISPR/Cas system that is specific for the cleavage sequence to be excised by insertion of the desired sequence into the target nucleic acid;

e) expressing the CRISPR/Cas system that is specific for the recombineering cleavage sequence to effect release of the recombineering segment from the recombineering plasmid;

f) maintaining the cells under conditions that permit viable cells to continue to live until recombineering insertion of the recombineering segment has occurred;

g) expressing the CRISPR/Cas system that is specific for the cleavage sequence to be excised via recombineering;

h) maintaining the cells under conditions that permit viable cells to continue to live until cleavage of cleavage sequences on the target nucleic acid has occurred; and i) selecting for recombinant cells that survive the CRISPR/Cas cleavage event at the target nucleic acid sequence; and Preferably steps a)-i) are repeated one or more times using the recombinant cell produced in step i) as the host cell for step a) of the following round;

wherein multiple, site-specific insertions of recombineering segments into the target nucleic acid creates a nucleic acid having a desired sequence.

In one embodiment, expression of the CRISPR/Cas system is regulated by one or more inducible promoter/repressor mechanisms. Preferably the host cells comprise a nucleic acid encoding a CRISPR/Cas system that is specific for the recombineering plasmid cleavage sequence and a nucleic acid encoding a CRISPR/Cas system that is specific for the cleavage sequence to be excised by insertion of the desired sequence into the target nucleic acid, and steps c) and d) are not practiced. Also preferably each of the nucleic acids encoding a CRISPR/Cas system further comprises a coding sequence for a selectable marker, each selectable marker being different than the other, to allow for selection, prior to expression of the CRISPR/Cas systems, for host cells containing both nucleic acids.

As an example of implementing the method in the same system, and in an embodiment where a single pre-defined cleavage sequence is targeted as the sequence to be removed/cleaved, in a first round, the CRISPR/Cas9 system of S. thermophilus is used to cleave target DNA at a sequence specific for CRISPR spacer sequence "1" (arbitrarily assigned for the purpose of this explanation). In a second round, the CRISPR/Cas9 system is used to cleave target DNA at a sequence specific for CRISPR spacer sequence "2" (arbitrarily assigned for the purpose of this explanation). And, in a third round, the CRISPR/Cas9 system is used to cleave target DNA at a sequence specific for CRISPR spacer sequence "3" (arbitrarily assigned for the purpose of this explanation). Et cetera. Each round uses the same CRISPR/Cas9 system; the difference being that, for each round, the spacer sequence in the CRISPR array is altered to change the specificity to the appropriate target nucleic acid cleavage sequence.

In other embodiments, cleavage sequences for two or more different dsDNA CRISPR/Cas systems are identified (or engineered, as discussed below). This step can be accomplished in any number of ways, as will be immediately apparent to the skilled artisan. However, it is envisioned that the most straightforward way is to consult one or more nucleic acid databases to determine the natural sequence of a site of interest and then determine if a cleavage site sequence exists within that site. According to the current state of the art, substantially all genomic sites of interest have been defined and their sequences determined. However, if for some reason a particular site is desired, and the sequence not currently known, it is a routine matter to isolate and sequence the site to determine the sequence and thus determine if a pre-selected cleavage sequence is present. As mentioned or alluded to above, various dsDNA cleaving CRISPR/Cas systems have been characterized, and it is assumed that many more will be characterized in the future. In either case, the skilled artisan can easily determine the functional requirements for known systems and newly discovered systems with routine investigation, then identify (or engineer) sequences on target nucleic acids that are cleavable by any system.

As a general consideration, identification and/or creation on a target nucleic acid of a complete cleavage sequence for a natural CRISPR/Cas system is not critical to practice of the invention. Rather, it is typically sufficient to identify (or engineer) a PAM sequence within a pre-determined site on the target nucleic acid, engineer a spacer sequence in a CRISPR array that is identical to the 30 nucleotides 5' of the PAM, and insert the spacer sequence between two repeat sequences in the CRISPR array, thus creating an artificial CRISPR cleavage guide that is specific for the sequence on the target nucleic acid. In other words, in embodiments of the invention, the step of identifying a dsDNA CRISPR/Cas cleavage sequence at a pre-determined site on a target nucleic acid can be accomplished by identifying the 30 nucleotides 5' of a PAM sequence that is present on the target nucleic acid, then engineering a CRISPR array to include those nucleotides as a spacer sequence. The method of the invention contemplates delivery of the CRISPR/Cas system to host cells on a plasmid or other delivery or expression vector. As such, the sequence of the CRISPR array can be modified/engineered as desired using common molecular biology techniques routinely used on extrachromosomal nucleic acid delivery and expression vectors.

Stated another way, and with general reference to FIG. 1, in preferred embodiments, a spacer sequence of a CRISPR array to be used in the present method is engineered to match a pre-defined cleavage sequence already present in the target nucleic acid (either naturally or as a result of a prior recombineering/cleavage/selection event), which is adjacent to a PAM sequence (which is present either naturally or as a result of a prior recombineering/cleavage/selection event), where the PAM sequence is functional for the CRISPR/Cas system being used. More specifically, most CRISPR/Cas systems studied to date target several different sequences for cleavage, the target cleavage sequences corresponding to the various spacer sequences in the CRISPR array, which are ultimately derived from foreign sequences that the host has identified as targets for cleavage and removal from the cell for defense purposes. Because the spacers tolerate variation in sequence in order to target multiple invading sequences, one can alter, mutate, or "program" the spacers of a CRISPR array to have one or more synthetic, mutated, or engineered spacer sequences that correspond (i.e., can hybridize to under physiological conditions) to one or more cleavage sequences in a target nucleic acid. In essence, one can engineer the CRISPR array sequence, and in particular a spacer sequence, of a pre-selected CRISPR/Cas system to effectively convert a sequence present on a target nucleic acid into a pre-defined cleavage sequence for the CRISPR/Cas system. Because CRISPR/Cas systems are known to be able to accommodate numerous spacer sequences within their CRISPR arrays, the number of engineered spacer sequences, and thus the number of pre-defined cleavage sequences on the target nucleic acid, is very large. In exemplary embodiments, a CRISPR array includes at least two or more spacer sequences, although the invention contemplates having only one in an array. The only limitation is that the site on the target nucleic acid must have a suitable PAM sequence present. Because the CRISPR/Cas system is typically delivered to a host cell in the form of an engineered vector (e.g., plasmid construct), it is often easier to engineer the vector sequence to match the target nucleic acid sequence than to engineer the target nucleic acid sequence to match the vector sequence. Therefore, in preferred embodiments, the nucleotide sequence of the CRISPR/Cas system, and in particular the spacer sequence, is engineered to interact with a host nucleic acid sequence rather than the opposite.

As mentioned above, rather than engineering a spacer sequence to match a naturally occurring sequence that is 5' to a PAM sequence, the practitioner may engineer a cleavage sequence into the site of interest on the target nucleic acid. As with engineering a spacer sequence on a plasmid vector, introduction of a cleavage sequence into a target nucleic acid can be accomplished in any number of ways with routine work, and the skilled artisan is free to select a suitable way depending on any number of considerations. It is envisioned, however, that mutagenesis, for example site-directed mutagenesis, will be used to engineer the cleavage sequence. As detailed in (10) and as discussed above, certain nucleotides in the PAM region and in the 3' region of the spacer are important for high-efficiency cleavage of dsDNA in a model system. As such, the skilled artisan would know to ensure that a competent PAM region and 3' region of the spacer be present.

The method of the invention further includes obtaining a recombineering segment that is, over at least a part of its sequence, homologous or otherwise sufficiently identical to a target nucleic acid sequence at a site where homologous recombination via recombineering is desired to allow for recombination using a recombineering system (the site is referred to herein as a "pre-determined site"). The pre-determined site can be any number of nucleotides in length as long as the length is sufficient to allow for homologous recombination using a recombineering system. In addition to having sequences sufficient for recombination, the pre-determined site comprises a cleavage sequence for a pre-determined dsDNA CRISPR/Cas cleavage system, which has been pre-selected, as described above. Using nucleic acid database information, by performing nucleotide sequencing, or by engineering the sequence, a pre-determined site can easily be identified and a recombineering segment made that includes sufficient nucleotide sequence identity to allow for a recombineering event to occur so as to replace a sequence present on the target nucleic acid with a desired sequence. As should now be evident, in addition to sequences sufficient for recombination with the target site, the recombineering segment includes a sequence that the practitioner desires to be inserted into the target nucleic acid (referred to herein as a "desired sequence"). When inserted into the target nucleic acid by homologous crossing-over, the desired sequence excises the pre-defined cleavage site from the target nucleic acid (e.g., host cell genome), thus rendering the site resistant to cleavage by the selected CRISPR/Cas system. To be clear, it is to be understood that, as used herein, the term "recombineering segment" means a nucleic acid that contains sufficient sequence identity with a pre-determined sequence of a target nucleic acid for homologous recombination to occur between the recombineering construct and the pre-determined sequence on the target nucleic acid such that a desired sequence is inserted into the target nucleic acid. Because the sequences surrounding each pre-defined cleavage sequence to be removed will often be different, and because each desired sequence will often be different in sequence from other desired sequences, in embodiments, there is one recombineering segment for each pre-defined cleavage sequence to be removed. However, in certain embodiments, such as those in which multiple identical desired sequences are to be inserted into a target nucleic acid that contains multiple repeats of a particular sequence, multiple different pre-defined cleavage sequences can be removed by recombineering segments having the same sequence. At times it can be preferable to use two or more cleavable sites for each inserted segment, as multiple sites might be cleaved more efficiently.

The act of obtaining a recombineering segment can be any act that results in the practitioner being in possession of the recombineering segment. It thus may include having someone make the recombineering segment and provide it to the practitioner, such as by ordering the segment from a commercial vendor that fabricates nucleic acids. Alternatively, the practitioner may make the recombineering segment himself. Production of nucleic acids, including but not limited to linear dsDNA molecules (such as a recombineering segment according to the present invention) and delivery/vector molecules for molecular biology purposes (such as a plasmid containing a CRISPR/Cas construct according to the present invention) is routine in the art, and any method for producing such nucleic acids can be used. Generally, chemical synthesis methods or molecular biology methods can be used, the particular method being selected based on the size of the construct desired. As is known in the art, in general, shorter constructs can be made cost-effectively and accurately using chemical synthesis methods whereas longer constructs are more amenable to production using molecular biology techniques.

The method of the invention also includes introducing a recombineering segment into the host cell that contains the target nucleic acid. The step of introducing the construct into a host cell can be any action that results in the desired effect. It thus can be accomplished by any suitable method known in the art for introduction of linear or circular nucleic acids (dsDNA, ssDNA, ssRNA, etc.) into a cell, including, but not limited to, standard transformation and transfection methods. Typically, the recombineering segment is in the form of a linear dsDNA molecule. However, in embodiments, the recombineering segment is in the form of a closed-circular nucleic acid, such as a dsDNA plasmid, from which the linear recombineering is removed such as by double-stranded cleavage of the plasmid at appropriate cleavage sites by restriction endonuclease(s). The skilled artisan is well aware of routine techniques to introduce all manner of nucleic acids into host cells, including prokaryotic (e.g., eubacterial) host cells. As such, a description of such techniques is not required herein.

The method of the invention also contemplates a recombinant host cell that includes a CRISPR/Cas system of the invention. According to the method, such a recombinant host cell can either be provided to the practitioner, for example by a commercial provider, or can be created by the practitioner using routine techniques known and widely and routinely practiced in the art to introduce the CRISPR/Cas system into the host cell. In some embodiments, multiple CRISPR/Cas systems are introduced into a single host cell, each CRISPR/Cas system having specificity for pre-defined cleavage sequences not being specified by any other CRISPR/Cas system. In these embodiments, it is preferred that expression of each different CRISPR/Cas system be under the control of a different controlling mechanism (e.g., different inducible or repressible promoters). In this way, successive rounds of recombineering/cleavage/selection can be performed without the need to transform selected cells after each round with a plasmid containing a different CRISPR/Cas system. Instead, the practitioner would simply need to expose the recombinant cell to the proper conditions for expression of only the CRISPR/Cas system desired. Many tightly-controlled promoter systems are known in the art, non-limiting examples of which being: the Tet control system, the arabinose control system, and the rhamnose control system.

As should be clear from the disclosure above, the method of the invention includes introducing at least one CRISPR/Cas system into a host cell. As discussed above, the dsDNA CRISPR/Cas cleavage system has been well defined, and the parts that are required, and are not required, for dsDNA cleavage defined. The present invention is preferable practiced with only those portions of the CRISPR/Cas system that are required for dsDNA cleavage. However, it can also be practiced with additional features of the CRISPR/Cas system or additional features derived from one or more other systems that are useful in molecular biology applications.

The method of the invention further includes maintaining the cell in a viable state until recombineering insertion of the recombineering segment(s) into the target nucleic acid has occurred, and CRISPR/Cas cleavage of the pre-defined cleavage sequences has occurred. While not required, to effect high levels of recombineering, in some embodiments it is preferred to delay introduction and/or expression of the CRISPR/Cas system as compared to introduction and/or expression of the recombineering segment. This can be accomplished, among other ways, by sequential introduction of the recombineering segment and the CRISPR/Cas system into the host cell, or by providing transcription and/or translation control sequences to control the timing of transcription and/or translation of one or the other within the host cell. Non-limiting embodiments relating to this concept are provided below.

The act of maintaining the recombinant cells in a viable state includes any act that achieves the stated result. Those of skill in the art of molecular biology are well aware of the appropriate environments that are suitable for host cells, which are in turn recombinant cells once exogenous nucleic acid is introduced into them, encompassed by the present invention. That is, each host cell contemplated by the present invention has been characterized, either directly or by reference to a closely related organism, with respect to environmental conditions (e.g., incubation temperature, growth media, atmosphere) that can be used to maintain the cell in a viable state while internal biochemical processes occur, including introducing a desired nucleic acid sequence into a target nucleic acid (e.g., recombineering) and endonucleolytic cleavage of a target nucleic acid by a dsDNA cleaving agent (e.g., CRISPR/Cas cleavage of dsDNA). As a non-limiting example, one can incubate a host $E.$ $coli$ under the following conditions: incubation for 8-24 hours in LB (Luria broth) at 25-39° C., preferably 37° C. Further, it should be recognized by the skilled artisan based on the teachings herein that, at least for the $S.$ $thermophilus$ CRISPR/Cas9 system, the $E.$ $coli$ host cell is preferably deficient for homologous recombination-based DNA repair pathways in order to achieve efficient selection. recA deletion would disable all repair pathways. However, recA is a required function for recombineering. Deletion of recB (recBC pathway) and/or components of the recF pathway (including recJ) is therefore preferable. In developing this invention, experimental data demonstrating the deletion of recN (in the recF DNA repair pathway) is beneficial for efficient selection in near wild type $E.$ $coli$ cells (data not shown herein). It is to be noted that the cell line used to demonstrate efficient selection by Cas9 is deficient in both the recB as well as the recF repair pathways. It is however not useful for recombineering as the strain does not tolerate the λ-red/gem expression plasmid.

Yet further, the method of the present invention includes the step of selecting for recombinant cells that survive the CRISPR/Cas cleavage event. The skilled artisan is well aware of various schemes for selecting recombinant cells that have undergone nucleic acid insertion, and any of those schemes can be used in this invention. However, a more elegant scheme is provided herein, which, while not always being completely effective, allows for sufficient enrichment of desired recombinant cells to make the method highly efficient and advantageously practiced to easily obtain, with routine screening by plating of treated cells, a desired recombinant cell. In brief, and as discussed above, the method of the invention uses a scheme for identifying and selecting desired recombinants that relies on cleavage of double-stranded target nucleic acid, and in particular dsDNA, by components of one or more CRISPR/Cas systems, at pre-defined cleavage sequences on the target nucleic acid. Double-stranded cleavage is indicative of a cell that has had one or more failed recombineering events, thus identifying cells that are not recombinant cells of interest to the practitioner. Further, double-stranded cleavage of a prokaryotic host chromosome will result in a high likelihood of death of the cell. As such, selection for successful recombineering events is a facile matter by simply plating a population of treated cells on an appropriate solid medium (e.g., an agar-based petri plate medium). In such a selection method, a high proportion, if not all, colonies that grow on the solid medium will represent recombinant cells that have had all pre-defined cleavage sequences removed as a result of a recombineering event. It is, of course, a simple matter given today's technology, to confirm whether a selected recombinant cell has the expected mutations/sequences within the target nucleic acid.

Between rounds, the CRISPR/Cas expression plasmid should be removed so that its encoded products do not interfere with the next round of recombineering/cleavage/selection. The CRISPR/Cas expression plasmid can be eliminated by several methods. The preferred method is the use of a temperate sensitive replicon, such as the tsCS101 replicon. The plasmid is stable at lower temperatures (e.g., less than 35° C.), but fails to efficiently replicate at higher incubation temperatures (e.g., more than 39° C.). The elimination can occur either directly (e.g., the CRISPR/Cas system is placed on a plasmid containing the ts-amplicon) or indirectly using a plasmid that requires a dedicated replication protein and placing this replication protein in trans on the temperature sensitive replicon. An example of such a replicon would be the pR6K plasmid. Alternatively, replicons requiring a dedicated replication protein can be eliminated by controlling expression of the replication protein using a regulatable promoter.

The method of the invention can be practiced up to this point to generate recombinant cells that contain target sequences that have been mutated to include multiple desired sequences, based on a single pre-defined cleavage sequence or more than one different pre-defined cleavage sequences present on a target nucleic acid. However, the method is more advantageously practiced by taking a recombinant cell produced by practicing the steps that effect recombineering/cleavage/selection, and repeating those steps one or more times, each on successively produced recombinant cells. When additional rounds of recombineering/cleavage/selection are practiced, the method includes the following feature: at least one round beyond the first includes the use of at least one recombineering segment that comprises at least one sequence that is suitable for homologous recombination with the target nucleic acid at a site that was introduced into the target nucleic acid as a result of a previous round of recombineering/cleavage/selection. In this way, multiple engineered sequences, having known and desired sequences, can be introduced into a target nucleic acid (e.g., a host cell chromosome), and then linked, by excision of intervening sequences. The method thus allows the practitioner to design and create, in vivo, a desired nucleotide sequence at a desired site in a target nucleic acid. This is in contrast to methods known in the art, which allow for one or more insertions into a target nucleic acid, but no coordinated production of large engineered sequences.

As should be apparent at this point, the invention includes recombinant cells that contain engineered sequences, which can be completely engineered to contain only exogenously-supplied sequences, or partially engineered (containing some exogenous sequences and some sequences that were originally present on the target nucleic acid), and which can be of a relatively long length, up to or exceeding 10 kb, 20, kb, 30 kb, 40 kb, 50 kb, 60 kb, 70 kb, 80 kb, 90 kb, 100 kb, or longer. Such cells are enabled by the in vivo engineering of long sequences using the method of the invention. In addition, such cells can be of any type in which a double-stranded break in a DNA sequence results in cell death (i.e., prokaryotic or viral).

EXAMPLES

The invention will be further explained by the following Examples, which are intended to be purely exemplary of the invention, and should not be considered as limiting the invention in any way.

Example 1

Practice of a Two-Round Production Method Based on Two Pre-Defined Cleavage Sequences and a CAS9 System Because bacteria typically are not able to efficiently repair DNA double strand breaks (such as those generated by the CRISPR/CAS9 system), the present invention is easily practiced in bacteria, with a target nucleic acid being the bacterial chromosome. According to the present invention, the presence of any DNA sequence adjacent to a PAM element (in a CAS9-containing system, either TGG or NGGNG) can be specifically targeted to become a negative selectable (e.g., lethal) marker in the presence of a CAS9 system programmed to cleave that sequence. In the presence of the programmed CAS9 system, the host cell is expected to survive only if the targeted DNA sequence on the bacterial chromosome is replaced as the consequence of a successful recombineering event, and thus the protected from cleavage. In embodiments, the disclosed method involves cloning of at least one spacer sequence flanked respectively by 2 repetitive elements into a functional CRISPR/Cas9 expression vector and delivery of this vector into a host cell which is subject to recombineering and selection for the presence of the engineered CAS9/CRSPR expression vector.

Figure 2:
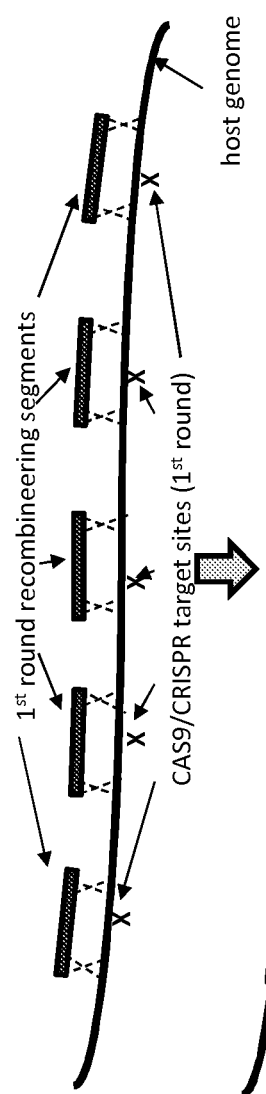
FIG. 2 is a diagram depicting an embodiment of the present invention in which in vivo engineering of a large, fully defined nucleic acid sequence is accomplished using two rounds of recombineering/cleavage/selection, and in which nucleic acids containing desired sequences (referred to herein at times as "recombineering segments") of the first round include homologous recombination sequences for the second round of recombineering, and in which at least two different CRISPR/Cas9 cleavage sequences are removed, one (or one set) in each round.
Figure 2:
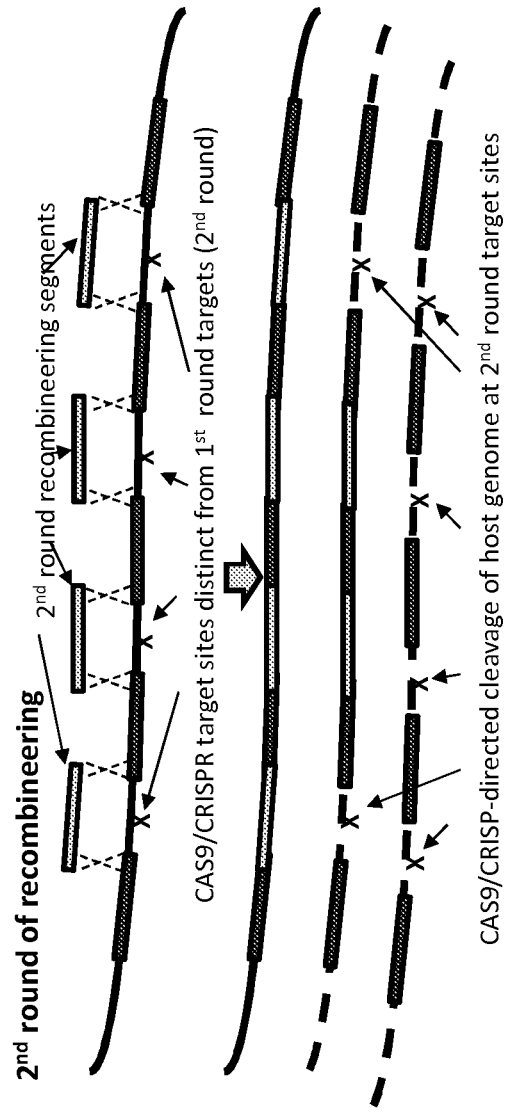

In the embodiment of the invention shown in FIG. 2, a two-round method of in vivo engineering of a large nucleic acid sequence according to the invention is depicted schematically. More specifically, the figure depicts in vivo assembly of a large or extremely large synthetic sequence by successive overlapping homologous recombination. Enabled by the potential scar-less selection of several simultaneous recombination events, a long, contiguous synthetic sequence is assembled directly in the host cell. In the first round, several recombineering segments with ends matching sequences in the host genome are inserted into the host cell. Recombination (via recombineering) of the segments with the host target results in excision of host sequences, some or all of which include CRISPR/Cas9 cleavage sequences. Cells that do not result in recombination events, or that result in only partial recombination events, are eliminated by CRISPR/Cas9 cleavage of the appropriate cleavage sequences on the target nucleic acid. One or more successful recombinant cells are selected. Survivors/successful recombinant cells of the first round of recombineering/cleavage/selection are then subjected to a second round of recombineering/cleavage/selection using recombineering segments with homologous ends to the segments introduced in the first round ofrecombineering. Cells that do not result in recombinants or show only partial recombination events during the second round are eliminated by CRISPR/Cas9 cleavage, and successful recombinants are selected.

It will be obvious to the skilled artisan that FIG. 2 is presented as a two-round selection process solely for the purpose of clarity and brevity. The skilled artisan will immediately recognize that additional cleavage sites for additional CRISPR/Cas specific sequences can be present on the target nucleic acid and be the subject of further rounds of recombineering/cleavage/selection to incorporate other sequences into the target nucleic acid. Further, additional features of other embodiments of the invention will be described below.

The intrinsic nature of the CRISPR/Cas unit allows tremendous flexibility and permits one to design a single round of recombineering/cleavage/selection that achieves simultaneous selection for recombination at several sites having the same or different cleavage sequences. Thus, several independent recombineering events can be implemented at several different sites on a target nucleic acid, and selected for in a single round. As the skilled artisan will recognize, the number of simultaneously selectable events in one round of selection is limited mostly by the efficiency of recombination. This invention does not address that parameter, but instead relies on the commercial standard for systems for recombination, which, in view of the advances provided by the present invention, are essentially equivalent.

As also will be recognized by the skilled artisan, for each system, a point of vanishing returns will be reached, at which point it is possible to continue to increase the number of independent recombination events based on different pre-defined cleavage sequences in a particular round, but the amount of work to identify recombinants having all of the desired insertions increases dramatically. At those points, it will be more efficient to perform multiple rounds of recombineering/cleavage/selection than to screen for recombinants having all of the desired insertions from a single round.

Integration by recombineering preferably requires that the integrating DNA be flanked by sequences sufficiently identical to sequences of the target nucleic acid to permit homologous recombination. Therefore, assembly of a large sequence typically is performed in successive rounds of recombineering, where the first round recombineering segments are linear molecules that have sequences (typically sequences at each end) that are homologous or sufficiently identical to the target nucleic acid (typically a host genome sequence) to effect recombination and to remove a pre-selected cleavage sequence as a result of that recombination. Subsequent round recombineering segments have sequences that are homologous or sufficiently identical to the target sequence, whether that sequence is a host sequence, a sequence introduced in a previous round of recombineering, or a combination of the two, to effect recombination and to remove a pre-selected cleavage sequence, where the pre-selected cleavage sequence is a different sequence than that removed in the immediately preceding round. In this way, each round of recombineering/cleavage/selection allows for selection based on a different cleavage sequence than the previous round. It also allows for engineering of pre-determined cleavage sequences for the next round that are identical to the previous round. In essence, it allows for a method in which a defined number of known cleavage sequences are used in alternating rounds of recombineering/cleavage/selection. As will be evident, where one or more of the rounds of recombineering/cleavage/selection uses multiple recognition/cleavage sequences, the next round will use pre-selected cleavage sequence(s) that differ from all of the sequences used in that round.

As discussed above, FIG. 2 depicts practice of the invention by way of an embodiment that uses a two-round process in which the second round utilizes recombineering segments that have homologous sequences that recombine with sequences present on the first round recombineering sequences. In the first round, a first set of cleavage sequences are removed, while in the second round, a second set of cleavage sequences are removed, resulting in creation of a large, defined sequence lacking both sets of cleavage sequences.

Example 2

Figure 3:
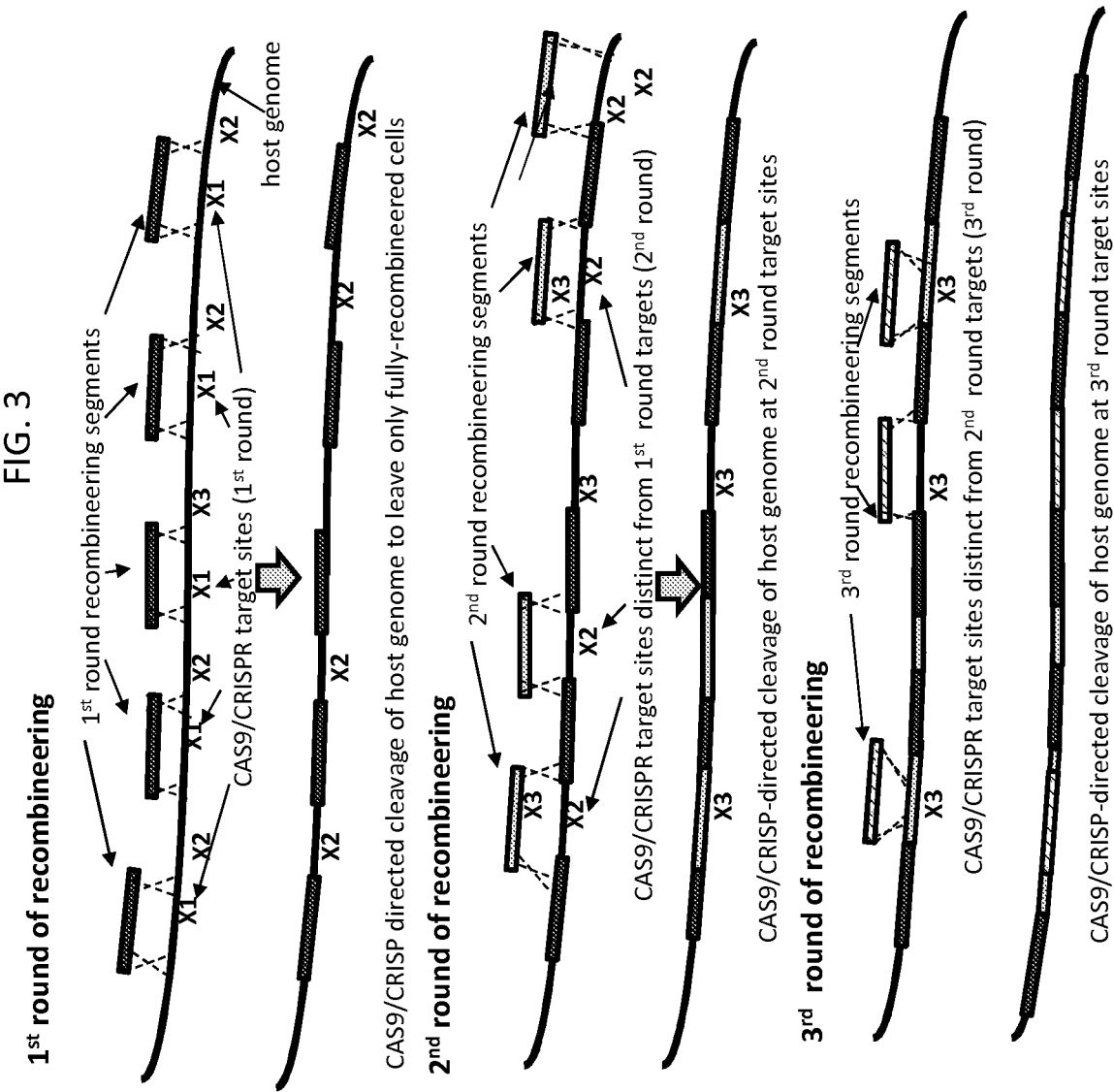
FIG. 3 is a diagram depicting an embodiment of the present invention in which in vivo engineering of a large, fully defined nucleic acid sequence is accomplished using multiple rounds of recombineering/cleavage/selection, and in which recombineering segments for one or more rounds include CRISPR/Cas cleavage sequences that are not present in the target sequence, thus introducing cleavage sequences that are not present in the original target nucleic acid sequence for additional rounds of recombineering/cleavage/selection.
Figure 4:
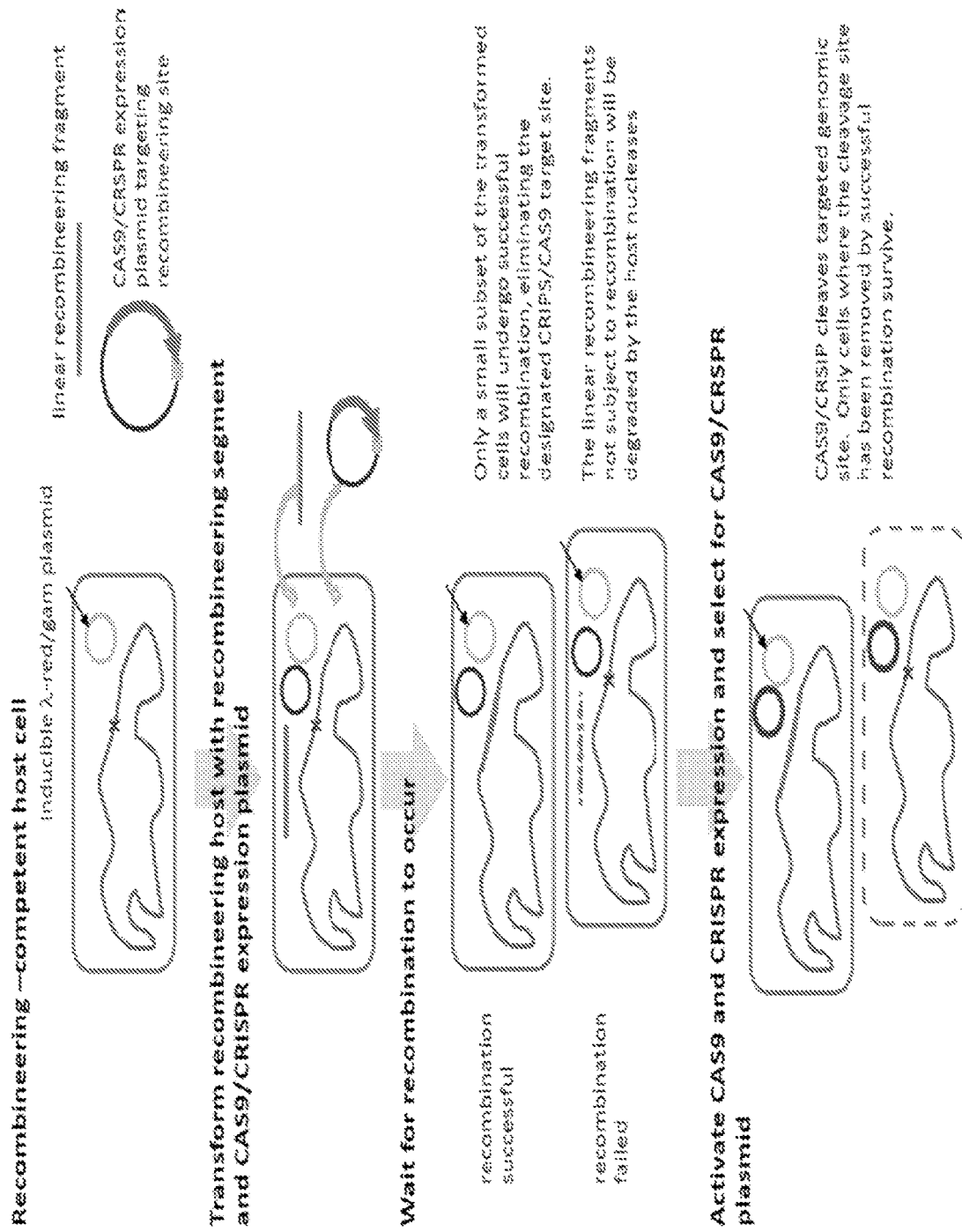
FIG. 4 is a diagram depicting an embodiment of the present invention that includes method steps for combined recombineering and CRISPR/Cas9 mediated target cleavage and selection using an inducible CRISPR/Cas9 system to enhance yield.

Multi-Round Engineering Method that Engineers Cleavage Sequences for Subsequent Rounds FIG. 3 depicts another embodiment of the method of the invention, which encompasses the embodiment of FIG. 2 but extends it to allow for additional control of the process for creating an engineered sequence in a target nucleic acid.

In the embodiment depicted in FIG. 3, recombineering in rounds subsequent to round 1 does not rely exclusively on recombination at sequences present in previously integrated recombineering segments to integrate the recombineering segments into the target nucleic acid. Rather, recombineering can rely on recombination with two unaltered host target nucleic acid sequences or with one host target nucleic acid sequence and one previously integrated recombineering segment. In other words, the embodiment depicted in FIG. 3 relates to the method of the invention as it relates broadly to a multi-round recombineering/cleavage/selection method in which, in each round, one or more pre-defined negative selection markers present on a target nucleic acid, where the negative selection markers comprise pre-defined CRISPR/Cas cleavage sequences, are eliminated as a result of successful integration of a recombineering construct, but in which the integration sites for each round beyond round 1 are not necessarily sites introduced into the target nucleic acid as a result of a prior round of recombineering. Typically, by the final round, all host sequences are removed from the engineered sequence. However, in some embodiments, it is preferred to leave host sequences intact, as they provide useful functional or structural features, such as promoters, terminators, and the like. As will be immediately apparent to the skilled artisan, such features can be identified with high accuracy based on sequence data alone, and engineering of recombineering constructs to design such host sequences into a final engineered sequences is well within the routine practice of such artisans.

Although it is envisioned that, in some embodiments, host sequences will be a part of the final engineered sequence, as a practical matter, it is likely easier to create a large sequence according to the invention by way of complete fabrication of the sequence. As such, in preferred embodiments, the method of the invention comprises, as a final round of recombineering/cleavage/selection, the use of recombineering constructs that have sequences that can homologously recombine with sequences introduced into the target nucleic acid as a result of one or more prior rounds of recombineering/cleavage/selection.

In vitro manipulation of DNA segments larger than 20 kb is difficult due to the inherent fragility of DNA, the inefficiency and relatively low fidelity of PCR, and the scarcity of usable unique restriction sites. The in vivo assembly technique described herein can be applied to a low copy plasmid or phagemid as the recombination target instead of the bacterial genome. If systems like cosmids or an equivalent system based on the P1 phage are used, large synthetic assemblies of >40 kb (cosmids) or >90 kb (P1 based phagemids) can be generated and packaged into phage particles (phagemids). Phage particles are generally easy to isolate and manipulate.

Example 3

Control of Timing of Expression of CRISPR/Cas System

Because CRISPR/Cas9-induced double strand breaks can be lethal to the recombineering host when the target nucleic acid is the host chromosome, some embodiments of the present invention control the timing of expression of the CRISPR/Cas system such that those components are not expressed until after the recombineering event has occurred. This can in principle be achieved by first performing the recombineering reaction (e.g., transforming a λ-red/gam competent host with a linear DNA recombineering segment), allowing the recombineered cells to recover and the recombination event to occur, and then delivering a CRISPR/Cas9 expression vector to the host cell in a second round of transformation. Recombineering using double stranded DNA is typically not very efficient (usually 1 recombinant/$10^4$ viable cells) and, aside from the inconvenience of producing competent cells from the recovery batch of the recombineering culture, transformation typically only introduces DNA into a small subset of a cell population. It is thus preferable to deliver the CRISPR/Cas9 expression vector along with the recombineering segments. However, because in these embodiments it is preferable that recombineering occurs before an active, host-directed Cas9 complex is formed, the formation of this complex has to be delayed.

Delayed formation of an active Cas9 complex can be achieved using several strategies that rely on delaying expression of the Cas9 protein, the CRISPR encoded crRNA, or both. For example, because an active CAS complex requires charging of the Cas protein with the CRISPR encoded crRNA, expression of the Cas9 protein, the crRNA, or both can be induced from a very tightly regulated promoter, and expression of the Cas9 protein, the crRNA, or both delayed until after the recombineering event has occurred. For an E. coli host, the rhamnose promoter can be sufficiently tight in regulation. Seeing that DNA cleavage by Cas9 requires the tracrRNA (9), that gene may be targeted for regulation alternatively or additionally.

Alternatively, the CRISPR/Cas9 expression construct can be made as an inactive precursor that is later converted to an active form in the recombineering host. This can be achieved using a slowly acting site-specific recombination system. If two site specific recombination sites are present on the same DNA strand in opposite orientations, the recombinase activity will result in the inversion of the intervening sequence. The site specific recombinase used in this context is preferably a system with an asymmetrical recognition site (such as ΦC31-integrase, λ-integrase or the E. coli FimB/E systems) to avoid reversion to the inactive form (symmetrical systems such as LoxP/Cre or Frt/Flp would result in constant toggling between the active and inactive orientations). The genes controlled by the recombinase system are preferably both Cas9 as well as the selectable marker to avoid background resulting from drug resistant clones where the recombinase-mediated activation has failed. An example of this set-up is given in FIG. 5.

Figure 5:
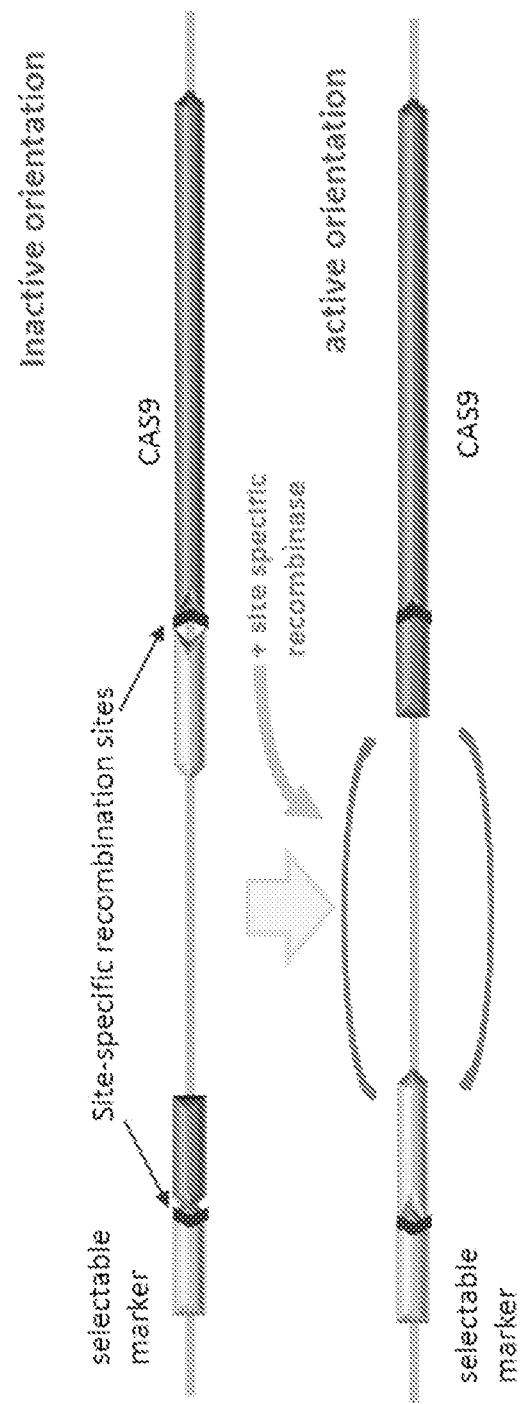
FIG. 5 schematically depicts an embodiment of the method of the invention in which activation of an inactive Cas9 precursor construct by site-specific recombination-mediated inversion occurs.

More specifically, FIG. 5 depicts activation of an inactive Cas9 precursor construct by site-specific recombination-mediated inversion. Formation of full length Cas9 is disrupted by separating the N-terminal end of the Cas9 from the C-terminal portion. When site specific recombination sites (such as lattr or FC31 integrase) are included in inverted orientation at the junction, expression of the cognate site specific recombinase will result in genomic inversion and subsequent restoration of the open reading frame. Recombination will leave a scar at the inversion site that will include extra amino acids (depending on the site, up to or around 10 amino acids). Thus, regions within the protein should be identified that accommodate the additional amino acids. If the same approach includes a selectable marker, successful inversion events can be directly selected for to avoid missed cleavage due to failed activation of Cas9.

Another alternate way by which a delayed activation of the CRISPR/Cas9 activity can be achieved is by insertion of an intein in the Cas9 protein. Inteins are protein sequences within a protein/peptide that remove themselves by an autocatalytic process. Intein removal is usually notoriously slow (>24 h), which is beneficial in this context. If the presence of an intein is disrupting Cas9 activity, removal of the intein should lead to slow re-activation, provided that the intein-containing polypeptide is stable in the host and the reconstituted protein is folded correctly.

Alternatively to the Cas9 gene the crRNA or the tracrRNA, both required for targeted DNA cleavage, can be targeted for regulation.

Example 4

Protection of the Cloning Host from Self-Cleavage

In embodiments, the method of the invention is dependent on the delivery of a CRISPR/Cas9 system as a functional expression plasmid. Construction of such a plasmid requires the use of a cloning host, typically a specialized E. coli strain, to produce sufficient plasmid for use in the method. One of the limitations in the plasmid preparation process is that the sequence targeted by the assembled CRISPR/Cas9 construct must not be present in the cloning host genome to prevent killing of the cloning host. This limits the sequences that can be targeted for negative selection by the CRISPR/Cas9 system, especially if the recombineering host is an E. coli strain as well. It is thus preferable that the expression construct is cloned as an inactive form.

As described above, there are several approaches by which this can be achieved. For example, expression of Cas9 can be tightly controlled and dependent on the presence of a specific inducer, such as the rhamnose promoter, the tet on/off promoter, or similar systems. Alternatively, the expression construct can be designed as an inactive precursor form that requires activation by inversion of a DNA segment by a site-specific recombinase provided by the recombineering host. This approach has the advantage that it solves the self-cleavage problem and can also help with the timing dilemma described above.

It is generally assumed that the crRNA is expressed from a separate promoter and thus acts as a separate expression unit from the Cas9 protein. It can be therefore expected that the CRISPR expression unit can be provided in trans on a separate expression plasmid. Separating the Cas9/tracrRNA and the crRNA expression units on separate plasmids also results in smaller constructs, which are generally easier to manipulate and can be a preferred solution.

Example 5

In Situ Assembly of Large Synthetic Sequences (Devices and Systems)

As a natural setup, most CRISPR/Cas systems target several different sequences for cleavage corresponding to the spacer sequences. The system can therefore be programmed with synthetic spacers corresponding to several sites in the host genome or another target nucleic acid, resulting in simultaneous selection for recombination at several sites. Thus, several independent recombineering events can be selected for at the same time. The number of simultaneously selectable events is expected to be limited mostly by the efficiency of recombination and will vary from system to system and host to host. Because selection using the CRISPR/Cas9 system allows scarless integration of any DNA sequence of choice, this approach can be used to generate large assemblies of DNA directly in the host genome or other target nucleic acids, avoiding the necessity to assemble and manipulate large constructs in vitro. Integration by recombineering requires that the integrated DNA is flanked by sequences homologous to the target nucleic acid. Therefore, assembly is performed in successive rounds of recombineering where the first round recombineering segments have extensions homologous to native sequences on the target nucleic acid and, in at least one subsequent round, one or more recombineering segments have extensions homologous to segments integrated in the first round of recombineering. The work flow for a two-step process is outlined in FIG. 2 and discussed above.

Example 6

Use of CRISPR/Cas9 to Produce Large Linear DNA Fragments In Vivo from Circular Plasmid Precursors λ-red/gam or recET based recombineering requires delivery of a linear piece of DNA into the recombineering host due to the requirement for generating 5'-recessed ends for binding of λ-single strand binding protein (beta). The dsDNA used in recombineering is typically generated by PCR, although DNA fragments generated by restriction digests can be used as well. The efficiency of recombineering is usually limited by the ability to introduce the recombineering fragment into the host and therefore the recombineering fragments are used at the highest concentration achievable. Nonetheless, only a small fraction of the transfected cells will receive the targeting DNA, thus limiting the frequency of successful recombineering events.

Figure 6:
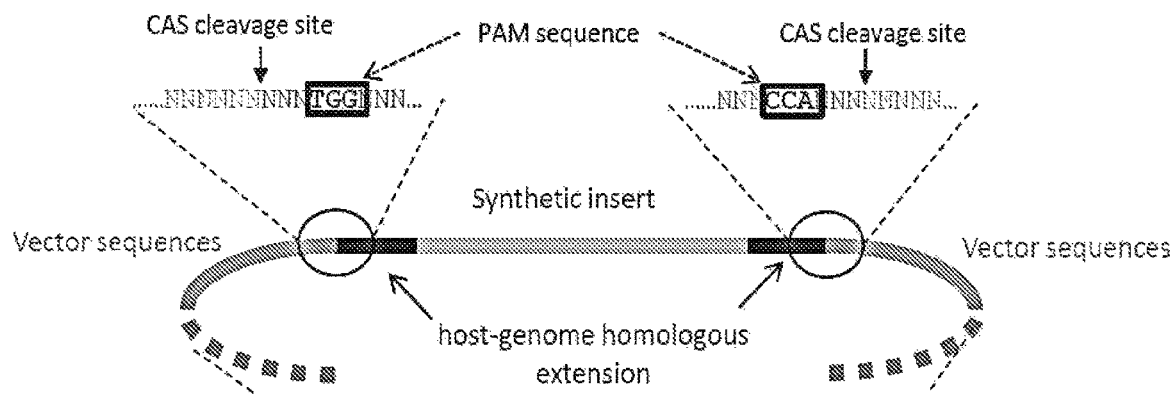
FIG. 6 schematically depicts the use of CRISPR/Cas9-mediated cleavage to release plasmid segments capable of recombineering. Panel A shows that efficient recombineering requires linear DNA with ends homologous to the targeted insertion sites. Linear DNA fragments can be released in vivo from a plasmid mediated by CRISPR/Cas9, provided a targetable PAM site exists 3 base pairs 3' to the cleavage site (SEQ ID NO: 8 or 9). Panel B shows a scheme for utilization of CRISPR/Cas9-mediated cleavage.
Figure 6:
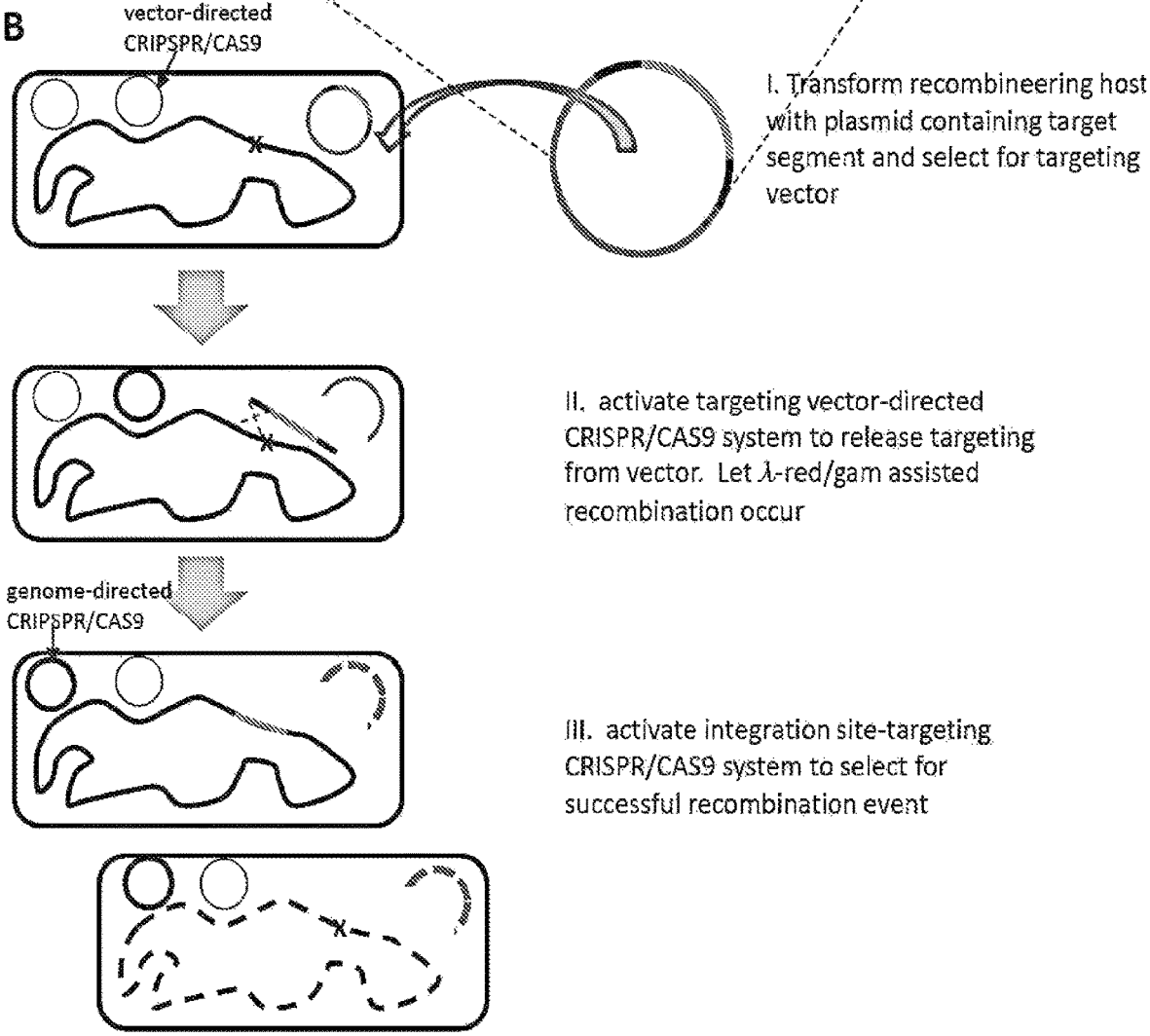

CRISPR/Cas9-mediated cleavage can be utilized to circumvent some of these limitations. The targeting segment can delivered on a plasmid and a population that contains a (multicopy) plasmid in every cell can be established by selection. The CRISPR/Cas9 system has been shown to generate blunt cuts 3 base pairs 5' to the corresponding PAM sequence (8,9). Thus, the targeting fragment can be precisely excised in vivo using Cas9 in conjunction with a CRISPR array targeting insert-flanking sequences. This approach ensures that all, or at least a high percentage, of cells in the population contain the targeting fragment in a processable form. It is also advantageous if large targeting fragments (>10 kb) are used because in vitro excision and purification is required. An outline of the procedure is shown in FIG. 6.

When this approach is used in conjunction with CRISPR/Cas9-mediated selection, the excision and selection directing CRISPR arrays should be expressed consecutively. This can be achieved by either introducing the selection CRISPR array after the excision array or controlling the selection- and the excision-crRNAs array by two orthogonal inducible promoters.

Example 7

Figure 7:
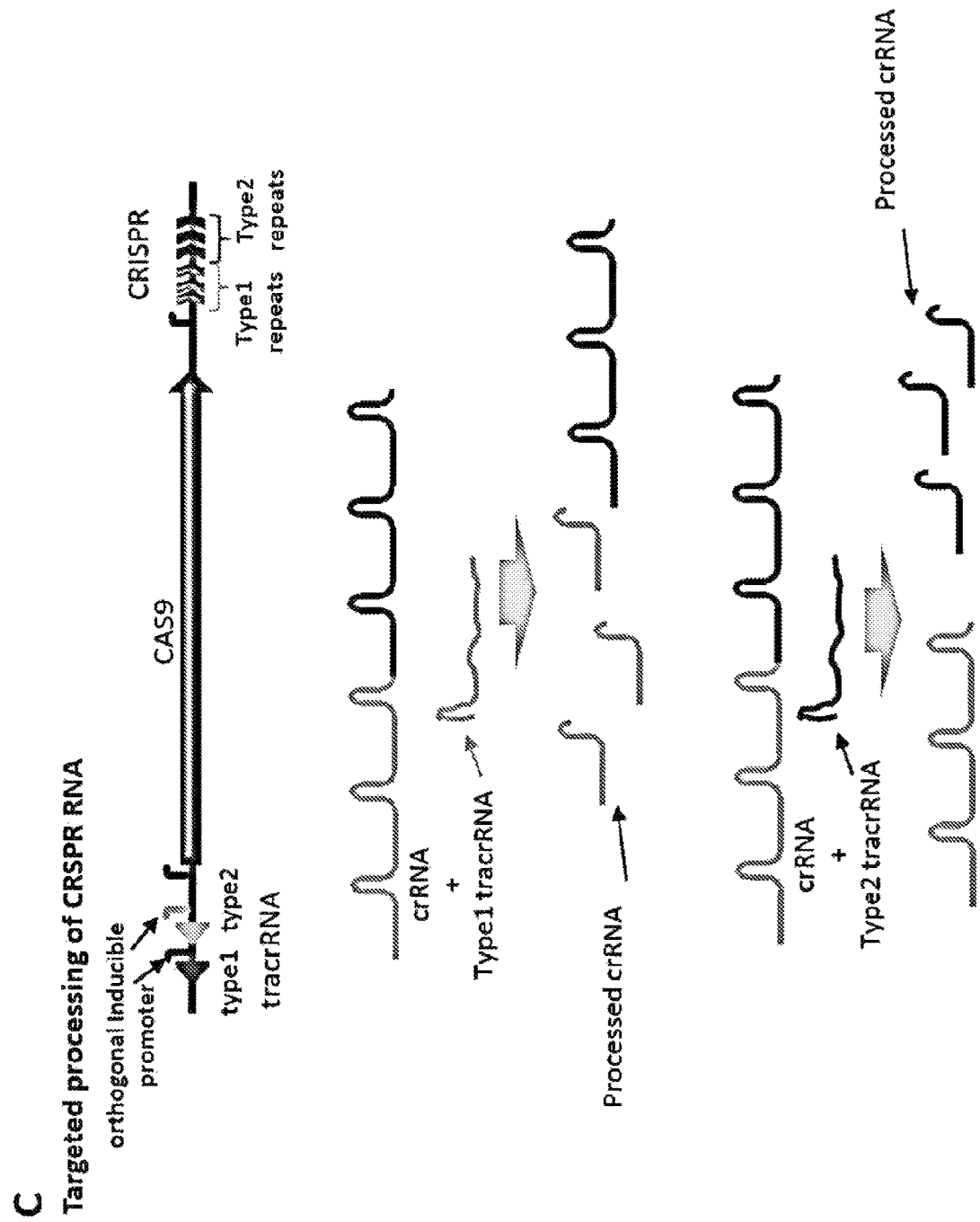
FIG. 7 depicts the use of orthogonal CRISPR repeat/tracrRNA pairs for selective activation of processing. Panel A shows an alignment of the CRISPR repeats from S. thermophilus (SEQ ID NO: 10) and S. pyogenes (SEQ ID NO: 2) and shows that the sequences are not stringently conserved. Panel B shows that the base pairing pattern between the CRISPR repeats (SEQ ID NOs: 11 and 13) and their respective tracrRNAs (SEQ ID NOs: 12 and 14) is conserved, indicating that CRISPR repeats and tracrRNA form a matching pair to enable processing. Panel C schematically shows that, by selective regulation of tracrRNAs from orthogonal tracrRNA/CRISPR repeats, specific segments of a CRISPR RNA transcript can be selectively targeted for processing.

Use of Orthogonal tracrRNA/CRISPR Pairs for Independent Activation of Different Guide RNAs from the Same CRISPR Array DNA cleavage by the CAS9 requires three components: the Cas9 protein, the CRISPR RNA, and the tracrRNA (a small, non-coding RNA partially complementary to the repeats in the CRISPR RNA). The tracrRNA is required for the RNAse III-mediated processing of the CRISPR RNA into the small guide RNAs as well as for the DNA cleavage by Cas9 (9). Alignment of the CRISPR repeats of the closely related CRISPR/Cas9 systems from *S. pyogenes* and *S. thermophilus* shows that the repeat elements are not perfectly conserved (see FIG. 7). However, the sequence differences between the CRISPR repeats are reflected in the respective tracrRNA, resulting in the same base pairing pattern between CRISPR repeat and tracrRNA in *S. pyogenes* and *S. thermophilus* (FIG. 7). This indicates that it is not the CRISPR repeat sequence, but the match to the tracrRNA, that is important for processing of the CRISPR transcript into mature guide RNAs. It is therefore possible to generate orthogonal pairs of CRISPR repeats and tracrRNAs where processing of the guide RNAs from the CRISPR transcript only occurs if the matching tracrRNA is expressed. One scheme for directing processing of specific CRISPR repeats from the primary CRISPR transcript is described in FIG. 7. Such setups are useful when consecutive targeting of different DNA sequences is required, such as described in the previous section.

Example 8

Use of CRISPR/Cas9 in Conjunction with Full Length recET

The methods described above are based, in part, on killing the host due to double strand cuts introduced in a host genome in the absence of a successful recombineering event. A recent publication demonstrates that recET mediated recombineering is strongly enhanced if a double strand break exists at the site targeted for recombination, provided full length recE is used (11). In conjunction with this recombineering method, the CRISPR/Cas9 system can be used to both enhance the recombineering frequency as well as subsequently select for the recombineering event. An additional advantage of this approach is that no efforts for tight temporal regulation of the Cas9 activity are required.

Example 9

Use of the Method to Select for Recombinants

Figure 8:
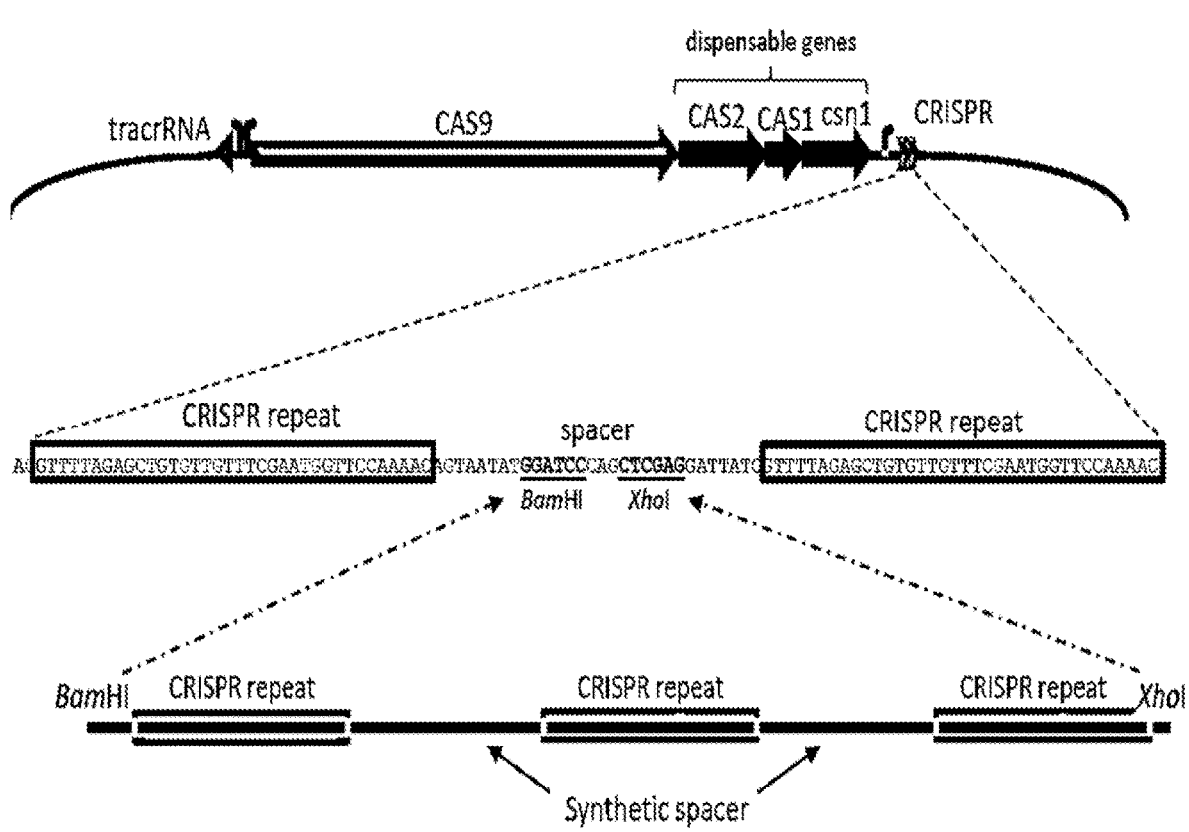
FIG. 8 shows schematically one way to design CRISPR/Cas9 expression vectors according to embodiments of the invention, which has a segment (SEQ ID NO: 15) containing an engineered spacer sandwiched between two CRISPR repeats. Also shown are four designs of synthetic spacers (SEQ ID NOs: 16-19).
Figure 8:
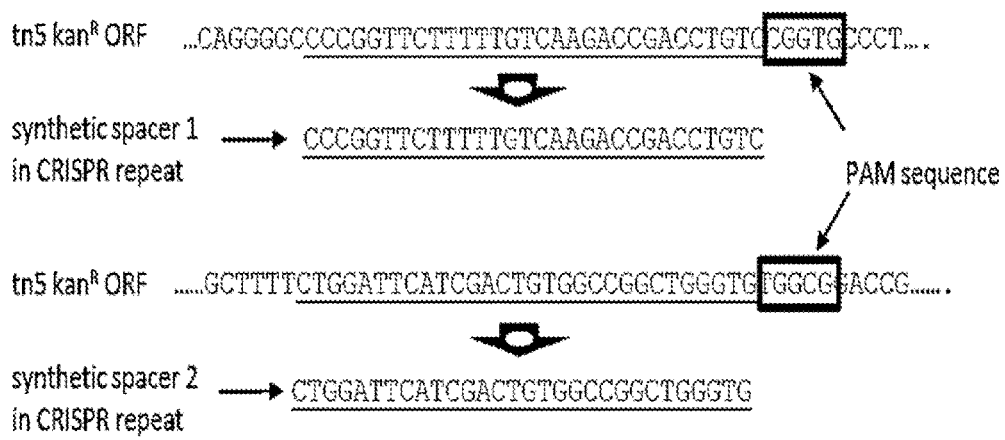

The CISPR3 of *Streptococcus thermophilus* was amplified in 9 overlapping segments by PCR using a genomic DNA prep of commercial Yoghurt (Trader Joe's Greek Yoghurt) as template. The region covered by the PCR fragments covers the CAS9, CAS1, CAS2, and csn1 gene as well as the 5' untranslated region up to the end of the ORF of the preceding gene and the 3' untranslated region up to the first CRISPR repeat sequence. A tenth segment containing two CRISPR repeats, a synthetic 30 nucleotide spacer with the BamHI and XhoI restriction sites for cloning of additional CRISPR repeats, and 57 base pairs of untranslated sequence 3' to the last natural CRISPR repeat was assembled synthetically from DNA oligos. The complete CRISPR3 cassette was assembled from these 10 segments and cloned into a pACYC 184-derived vector conferring chloramphenicol resistance under the control of the tet promoter using a specifically developed Quickchange Multisite site-directed mutagenesis kit (Agilent) chemistry-based cloning method. Mutations relative to the strain NDO3 reference sequence were removed using the Quickchange Multisite lightning site directed mutagenesis kit (Agilent). A map of the expression unit is provided in FIG. 8. The resulting construct still contains two mutations, one silent mutation at and one mutation located in the 3' untranslated region. Into this vector two synthetic spacer elements separated by CRISPR repeats where inserted into the BamHI and XhoI sites of the basic CAS9/CRISPR expression vector. The spacer sequences correspond to the tn5 kanamycin resistance marker at sites with reported PAM sequences.

The general outline of the process is depicted in FIG. 7, which shows that the CRISPR locus from *S. thermophilus* was cloned into a pACYC-based vector. The vector has a p15A origin of replication and confers chloramphenicol resistance. The natural CRISPR array was replaced with two CRISPR repeats and a synthetic spacer sequence containing unique BamHI and XhoI sites for cloning purposes. The resulting vector pLCR3 provides a Cas9 charged with one guide RNA that has no known natural target. The expression vector pLCR3-kanA, targeting the tn5 kanamycin resistance, marker was generated by inserting two additional CRISPR repeats with spacer sequences corresponding to selected tn5 kan$^R$ target sequences with adjacent PAM elements into the BamHI and XhoI sites of pLCR3. pLCR3-kanA provides a Cas charged with one of four guide RNAs, two corresponding to the tn5 kanamycin resistance marker and two with no known natural target.

When a target nucleic acid is part of a host cell genome, or the target site is on an extrachromosomal element that confers viability to the cell under selection pressure (e.g., a stably maintained plasmid conferring antibiotic resistance), CRISPR/Cas9-directed cleavage eliminates host strains having pre-defined cleavage sequences. The method of the invention relies on the fact that CRISPR/Cas9 directed cleavage of a target nucleic acid constitutes a lethal event in many, if not most or all, cells in which a pre-defined cleavage sequence is present. To verify that this is a valid concept, plasmids pLCR3 (containing no host directed spacer RNA in the CRISPR repeat) or pLCR3-kanA (containing two spacers directed against the tn5 kanamycin resistance marker) were used to transform either XL1-blue or SURE cells (both Agilent) and selected for chloramphenicol resistance encoded on the plasmids. XL1-blue is not targeted by either construct whereas SURE cells, which contain the tn5 kanamycin resistance marker in the host genome, are targeted for cleavage by pLCR-kanA but not pLCR3. XL1-blue is not targeted by either vector.

Figure 9:
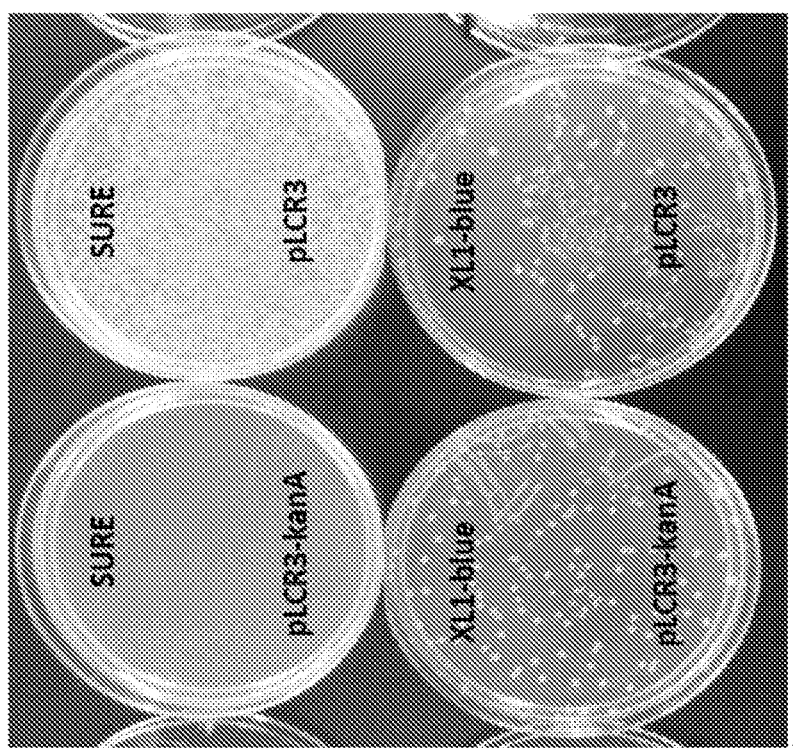
FIG. 9 shows the results of plating of cells subjected to a recombineering/cleavage/selection process, showing that CRISPR/Cas9 directed cleavage of a host genome kills the targeted host. The host strains SURE and XL1blue were transformed with the CRISPR/Cas9 plasmids pLCR3 (no targeted sequences) or 1CR3-kanA (targets tn5 kan$^R$ for cleavage). In the SURE strain that carries a tn5 kan$^R$ marker on the chromosome, only the non-targeting pLCR3, but not the tn5-kanR targeting pLCR3-kanA can be established. Both plasmids can be established with equal efficiency in XL1-blue, which does not contain target sequences for either vector.

As shown in FIG. 9, both plasmids can be established in XL1 blue but only the non-targeting plasmid pLCR3-kanA can be established in SURE cells, demonstrating that hosts containing CRISPR/CAS9-targeted sequences can be eliminated using this system.

Figure 10:
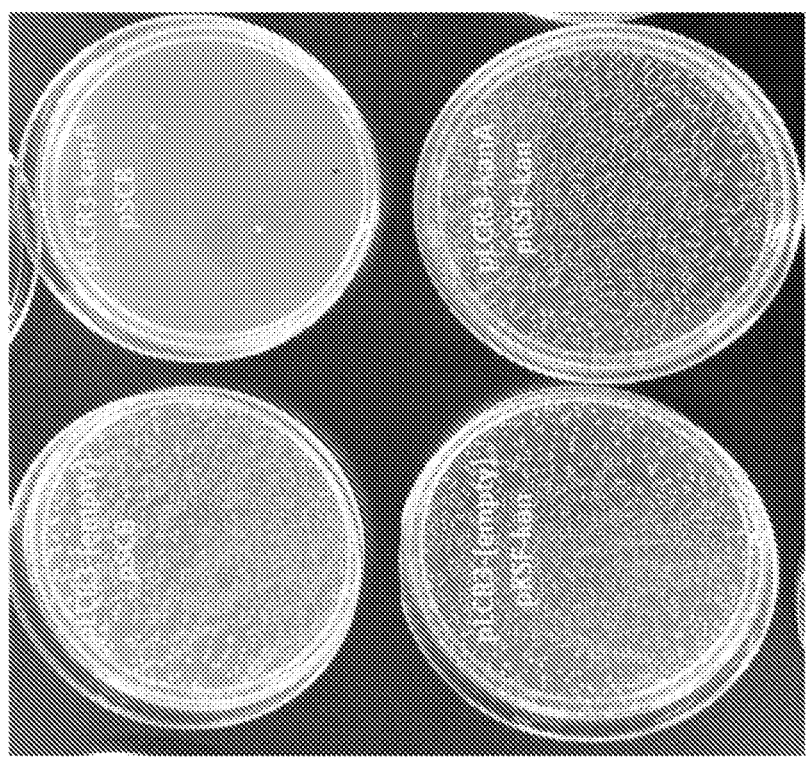
FIG. 10 shows the results of plating of transformed cells, indicating that the CRISPR/Cas9 system used in embodiment of the invention acts as a restriction system against targeted plasmids.

The functionality of CRISPR/Cas9 to act as a restriction system for DNA was verified by rendering XL1 blue cells containing either pLCR3 (non targeting) or pLCR3-kanA (targeting tn5 kan$^R$) chemically transformation competent and transforming both strains with either pSCB or pKSF-kan. Both plasmids are pBluescript based vectors carrying an ampicillin resistance marker and a kanamycin resistance marker. The kanamycin marker on pSCB is derived from tn5 which is targeted by pLCR-kanA whereas pKSF-kan carries a tn903 derived kanamycin resistance marker that is not targeted by pLCR-kanA. Transformants were selected for ampicillin resistance. As shown in FIG. 10, only pKSF-kan (not targeted) but not pSCB can be established in pLCR-kanA host cells, whereas both plasmids can be established in pLCR3 carrying host cells.

More specifically, FIG. 10 shows that the CRISPR/Cas9 system can act as a restriction system against targeted plasmids. XL1-blue host strains containing either pLCR3 (non-targeting CRISPR spacer) or pLCR3-kanA (tn5-kan$^R$ targeting CRISPR spacer) were transformed with the plasmids pSCB or pKSF-kan and were selected for ampicillin resistance. Both plasmids are high copy colE1 plasmids compatible with pLCR3 replication carrying the ampicillin resistance marker and a kanamycin resistance marker. pSCB carries a tn5 kan$^R$ marker that is targeted by pLCR-kanA whereas pKSF-kan carries a tn903-derived kan$^R$ marker that is not targeted. Only the not-targeted pKSF-kan but not the targeted pSCB can be established in the presence of pLCR3-kanA. The two colonies observed on the pLCR3-kanA/pSCB plate result from the loss of the pLCR3-kanA plasmid.

The skilled artisan will recognize from the results presented in this Example that the method of the invention can be used to create pre-defined cleavage sequences at any site or sites of interest in an engineered sequence, and then later use those sequences for controlled removal of intervening sequences. That is, the present method can be used to insert site-specific cleavage sites into a target nucleic acid, and those sites can be used in the same manner that commonly known restriction endonuclease recognition sites are used.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only.

REFERENCES

1. Datsenko, K. A., and Wanner, B. L., "One-step inactivation of chromosomal genes in *Escherichia coli* K-12 using PCR products", *Proc. Natl. Acad. Sci USA* 97: 6640 (2000).
2. Costandino N, and Court, D. L., "Enhanced levels of 1 Red-mediated recombinants in mismatch repair mutants", *Proc. Natl. Acad. Sci USA* 100: 15748 (2003).
3. Kolodner, R. et al., "Homologous pairing proteins encoded by the *Escherichia coli* recE and recT genes", *Mol. Microbiol.* 11:23-30 (1994).
4. Gust, B. et al., "1 Red-Mediated Genetic Manipulation of Antibiotic-Producing *Streptomyces*", *Adv. Appl. Microbiol.* 54: 107 (2004).
5. Katashkina, J. I. et al., "Use of the λ Red-recombineering method for genetic engineering of *Pantoea ananatis*", *BMC Mol. Biol.* 10:34 (2009).
6. Horvath, P. et al., "CRISPR/Cas, the Immune System of Bacteria and Archaea", *Science* 327: 167 (2010).
7. Garneau, J. E. et al., "The CRISPR/CAS bacterial immune system cleaves bacteriophage and plasmid DNA", *Nature* 468: 67 (2010).
8. Sapranauskas, R., et al., "The *Streptococcus thermophilus* CRISPR/CASA system provides immunity in *Escherichia coli*", *Nucleic Acids Res.* 39: 9275 (2011).
9. Jinek et al., "A programmable Dual-RNA-Guided DNA Endonuclease in Adaptive Bacterial Immunity", *Science Express*, 28 Jun. 2012.
10. Jiang, W. et al., "RNA-guided editing of bacterial genomes using CRISPR-Cas systems", *Nat. Biotechnol.* 29 Jan. 2013 (advance online publication), document doi: 10.1038/nbt.2508.
11. Fu, J. et al., "Full-length RecE enhances linear-linear homologous recombination and facilitates direct cloning for bioprospecting", *Nat Biotechnol.* 30: 440-6 (2012).

The invention claimed is:

1. A method for engineering into a bacterial host cell a nucleic acid having a desired sequence, said method comprising:
   a) identifying or creating a double stranded DNA CRISPR/Cas cleavage sequence at a predetermined site on a target nucleic acid in a bacterial host cell;
   b) obtaining a recombineering segment for the pre-determined site, where the recombineering segment comprises a sequence for insertion into the target nucleic acid and that, when the sequence is inserted into the target nucleic acid by homologous recombination, the insertion eliminates the cleavage sequence and wherein the sequence for insertion does not comprise a selection marker;
   c) introducing into the bacterial host cell the recombineering segment;
   d) if not already present in the bacterial host cell, introducing into the bacterial host cell a CRISPR/Cas system that is specific for the cleavage sequence, wherein the CRISPR/Cas system cleaves the cleavage sequence if no insertion of the sequence for insertion has occurred;
   e) maintaining the bacterial host cell in a viable state until recombineering insertion of the sequence for insertion and the CRISPR/Cas cleavage of the cleavage sequence has occurred;
   f) producing a recombinant cell which has integrated the sequence for insertion by plating and growing the cell of step e),
   g) repeating steps a)-f) one or more times using the recombinant cell produced in step f) as the bacterial host cell for step a) of the following round;
   wherein multiple, site-specific insertions of recombineering segments into the target nucleic acid creates a nucleic acid having a desired sequence.

2. The method of claim 1, wherein, after performance of steps a)-f) one time, each successive performance of steps a)-f) uses recombineering segments that include sequences for homologous recombination that recombine with sequences present in a recombineering segment used in a prior performance of steps a)-f).

3. The method of claim 1, wherein, after performance of steps a)-f) one time, at least one successive performance of steps a)-f) uses at least one recombineering segment that includes a sequence for homologous recombination that recombines with at least one sequence present in a recombineering segment used in a prior performance of steps a)-f).

4. The method of claim 1, wherein a recombineering segment used in one round of performance of steps a)-f) comprise a cleavage sequence for a subsequent round of performance of steps a)-f).

5. The method of claim 1, wherein, for each round of performance of steps a)-f), the cleavage sequence is different than the cleavage sequence used for the immediate prior round.

6. A recombinant cell made by the method of claim 5.

7. A method for engineering into a bacterial host cell a nucleic acid having a desired sequence, said method comprising:
   a) identifying or creating a double-stranded DNA CRISPR/Cas cleavage sequence at a predetermined site on a target nucleic acid in a bacterial host cell;
   b) obtaining a recombineering segment for the pre-determined site, where the recombineering segment comprises a sequence for insertion into the target nucleic acid and that, when the sequence is inserted into the target nucleic acid by homologous recombination, the insertion eliminates the cleavage sequence; and wherein the sequence for insertion does not comprise a selection marker;
   c) introducing into the bacterial host cell the recombineering segment;
   d) if not already present in the bacterial host cell, introducing into the bacterial host cell a CRISPR/Cas system that is specific for the cleavage sequence, wherein the CRISPR/Cas system cleaves the cleavage sequence if no insertion of the sequence for insertion has occurred;
   e) maintaining the bacterial host cell in a viable state until recombineering insertion of the sequence for insertion and the CRISPR/Cas cleavage of the cleavage sequence has occurred;
   f) producing a recombinant cell which has integrated the sequence for insertion by plating and growing the cell of step e).

8. The method of claim 7, wherein the CRISPR/Cas system is inducible and it is activated in step e).

9. The method of claim 8, wherein activating the CRISPR/Cas system that is specific for the cleavage sequence is accomplished by inducing an inducible promoter or de-repressing a repressible promoter.

* * * * *

SEQUENCE LISTING

<160> NUMBER OF SEQ ID NOS: 19

<210> SEQ ID NO 1
<211> LENGTH: 108
<212> TYPE: DNA

```
<213> ORGANISM: Streptococcus thermophilus

<400> SEQUENCE: 1
tacgaggttt tagagctgtg ttgtttcgaa tggttccaaa acagtaatat caaaaaagcc    60
cccttgatta tcgttttaga gctgtgttgt ttcgaatggt tccaaaac                108

<210> SEQ ID NO 2
<211> LENGTH: 36
<212> TYPE: DNA
<213> ORGANISM: Streptococcus thermophilus

<400> SEQUENCE: 2
gttttagagc tgtgttgttt cgaatggttc caaaac                              36

<210> SEQ ID NO 3
<211> LENGTH: 30
<212> TYPE: DNA
<213> ORGANISM: Streptococcus thermophilus

<400> SEQUENCE: 3
agtaatatca aaaagccccc cttgattatc                                     30

<210> SEQ ID NO 4
<211> LENGTH: 46
<212> TYPE: DNA
<213> ORGANISM: Escherichia coli
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(46)
<223> OTHER INFORMATION: n is a, c, g, or t

<400> SEQUENCE: 4
nnnnnnnnag taatatcaaa aagccccct tgattatcng gngnnn                    46

<210> SEQ ID NO 5
<211> LENGTH: 4
<212> TYPE: DNA
<213> ORGANISM: Escherichia coli
<220> FEATURE:
<221> NAME/KEY: misc_feature
<222> LOCATION: (3)..(3)
<223> OTHER INFORMATION: n is a, c, g, or t

<400> SEQUENCE: 5 ggng                                                                  4

<210> SEQ ID NO 6
<211> LENGTH: 3
<212> TYPE: DNA
<213> ORGANISM: Escherichia coli

<400> SEQUENCE: 6 tgg                                                                   3
```

```
<210> SEQ ID NO 7
<211> LENGTH: 11
<212> TYPE: DNA
<213> ORGANISM: Escherichia coli
<220> FEATURE:
<221> NAME/KEY: misc_feature
<222> LOCATION: (7)..(11)
<223> OTHER INFORMATION: n is a, c, g, or t

<400> SEQUENCE: 7
atctggnnnn n                                                          11

<210> SEQ ID NO 8
<211> LENGTH: 15
<212> TYPE: DNA
<213> ORGANISM: Artificial Sequence
<220> FEATURE:
<223> OTHER INFORMATION: CAS cleavage site
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 8
nnnnnnnnnt ggnnn                                                      15

<210> SEQ ID NO 9
<211> LENGTH: 14
<212> TYPE: DNA
<213> ORGANISM: Artificial Sequence
<220> FEATURE:
<223> OTHER INFORMATION: CAS cleavage site
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 9
nnnnnnnnac cnnn                                                       14

<210> SEQ ID NO 10
<211> LENGTH: 36
<212> TYPE: DNA
<213> ORGANISM: Streptococcus pyogenes

<400> SEQUENCE: 10
gttttagagc tatgctgttt tgaatggtcc caaaac                               36

<210> SEQ ID NO 11
<211> LENGTH: 50
<212> TYPE: RNA
<213> ORGANISM: Streptococcus pyogenes
<220> FEATURE:
<221> NAME/KEY: misc_feature
<222> LOCATION: (1)..(14)
<223> OTHER INFORMATION: n is a, c, g, or u

<400> SEQUENCE: 11
nnnnnnnnnn nnnnguuuua gagcuaugcu guuuugaaug gucccaaaac                50

<210> SEQ ID NO 12
```

-continued

```
<211> LENGTH: 111
<212> TYPE: RNA
<213> ORGANISM: Streptococcus pyogenes

<400> SEQUENCE: 12
auaaaaguua uaaaauaauu uuguuggaac cauucaaaac agcauagcaa guuaaaauaa      60
ggcuaguccg uuaucaacuu gaaaaagugg caccgagucg gugcuuuuuu u             111

<210> SEQ ID NO 13
<211> LENGTH: 42
<212> TYPE: RNA
<213> ORGANISM: Streptococcus thermophilus
<220> FEATURE:
<221> NAME/KEY: misc_feature
<222> LOCATION: (1)..(6)
<223> OTHER INFORMATION: n is a, c, g, or u

<400> SEQUENCE: 13
nnnnnnguuu uagagcugug uuguuucgaa ugguuccaaa ac                        42

<210> SEQ ID NO 14
<211> LENGTH: 113
<212> TYPE: RNA
<213> ORGANISM: Streptococcus thermophilus

<400> SEQUENCE: 14
aaaacuauau aauaauaauu gugguuugaa accauucgaa acaacacagc gaguuaaaau     60
aaggcuuagu ccguacucaa cuugaaaagg uggcaccgau ucggguguuu uuu           113

<210> SEQ ID NO 15
<211> LENGTH: 104
<212> TYPE: DNA
<213> ORGANISM: Artificial Sequence
<220> FEATURE:
<223> OTHER INFORMATION: Engineered spacer sandwiched by two CRISPR
      repeats

<400> SEQUENCE: 15
acgttttaga gctgtgttgt ttcgaatggt tccaaaacag taatatggat cccagctcga     60
ggattatcgt tttagagctg tgttgtttcg aatggttcca aaac                    104

<210> SEQ ID NO 16
<211> LENGTH: 46
<212> TYPE: DNA
<213> ORGANISM: Artificial Sequence
<220> FEATURE:
<223> OTHER INFORMATION: tn5 kanR ORF

<400> SEQUENCE: 16
caggggcccc ggttcttttt gtcaagaccg acctgtccgg tgccct                   46

<210> SEQ ID NO 17
<211> LENGTH: 30
<212> TYPE: DNA
<213> ORGANISM: Artificial Sequence
<220> FEATURE:
<223> OTHER INFORMATION: synthetic spacer 1 in CRISPR repeat

<400> SEQUENCE: 17
cccggttctt tttgtcaaga ccgacctgtc                                     30

<210> SEQ ID NO 18
<211> LENGTH: 46
<212> TYPE: DNA
```

```
<213> ORGANISM: Artificial Sequence
<220> FEATURE:
<223> OTHER INFORMATION: tn5 kanR ORF

<400> SEQUENCE: 18
gcttttctgg attcatcgac tgtggccggc tgggtgtggc ggaccg                46

<210> SEQ ID NO 19
<211> LENGTH: 30
<212> TYPE: DNA
<213> ORGANISM: Artificial Sequence
<220> FEATURE:
<223> OTHER INFORMATION: synthetic spacer 2 in CRISPR repeat

<400> SEQUENCE: 19
ctggattcat cgactgtggc cggctgggtg                                  30
```